United States Patent [19]

Mumford et al.

[11] 4,432,360

[45] Feb. 21, 1984

[54] INTERACTIVE PROGRAMMER FOR BIOMEDICAL IMPLANTABLE DEVICES

[75] Inventors: Van E. Mumford; Louis Sasmor, both of Miami; Edward A. Schroeppel, Miramar, all of Fla.

[73] Assignee: Cordis Corporation, Miami, Fla.

[21] Appl. No.: 281,011

[22] Filed: Jul. 6, 1981

[51] Int. Cl.³ .............................................. A61N 1/36
[52] U.S. Cl. ............................................ 128/419 PG
[58] Field of Search ................... 128/419 PG, 419 DT

[56] References Cited

U.S. PATENT DOCUMENTS

| | | | |
|---|---|---|---|
| 4,208,008 | 6/1980 | Smith | 371/15 |
| 4,245,641 | 1/1981 | Mann et al. | 128/419 PG |
| 4,305,397 | 12/1981 | Weisbrod et al. | 128/419 PT |

OTHER PUBLICATIONS

"Spectrax ™ Multi-Programmable Pacemaker Continues Clinical Evaluation", *Medtronic News*, Sep. 1979, pp. 12 and 13.

*Primary Examiner*—William E. Kamm
*Attorney, Agent, or Firm*—Kenway & Jenney

[57] ABSTRACT

A computer-controlled programmer having a user-interactive display is designed to control the parameters of a wide variety of implantable devices with different programming requirements. During programming, screen messages prompt the user to perform required actions by pressing lighted targets on the display screen. The programmer includes a console and a lightweight cable connected programming head. When the console is turned on, a self test routine automatically tests the programmer's batteries, memory banks and communications systems. For the communications test, the programmer employs a self-contained telemetry system which mimics the response of an implant. With certain implants, the programmer automatically changes programming options in response to information received from an implant as well as in response to selection of certain modes and lead configurations. The programmer software is designed to limit access to certain values and parameters which require the attendance of an authorized physician. Access to these non-routine programming functions is provided via a combination lock on the console. With implants having data telemetry, the programmer software is designed to confirm programming by comparing a stored replica of the originally transmitted programming data to an automatic echo of the programming data received by the implant.

16 Claims, 46 Drawing Figures

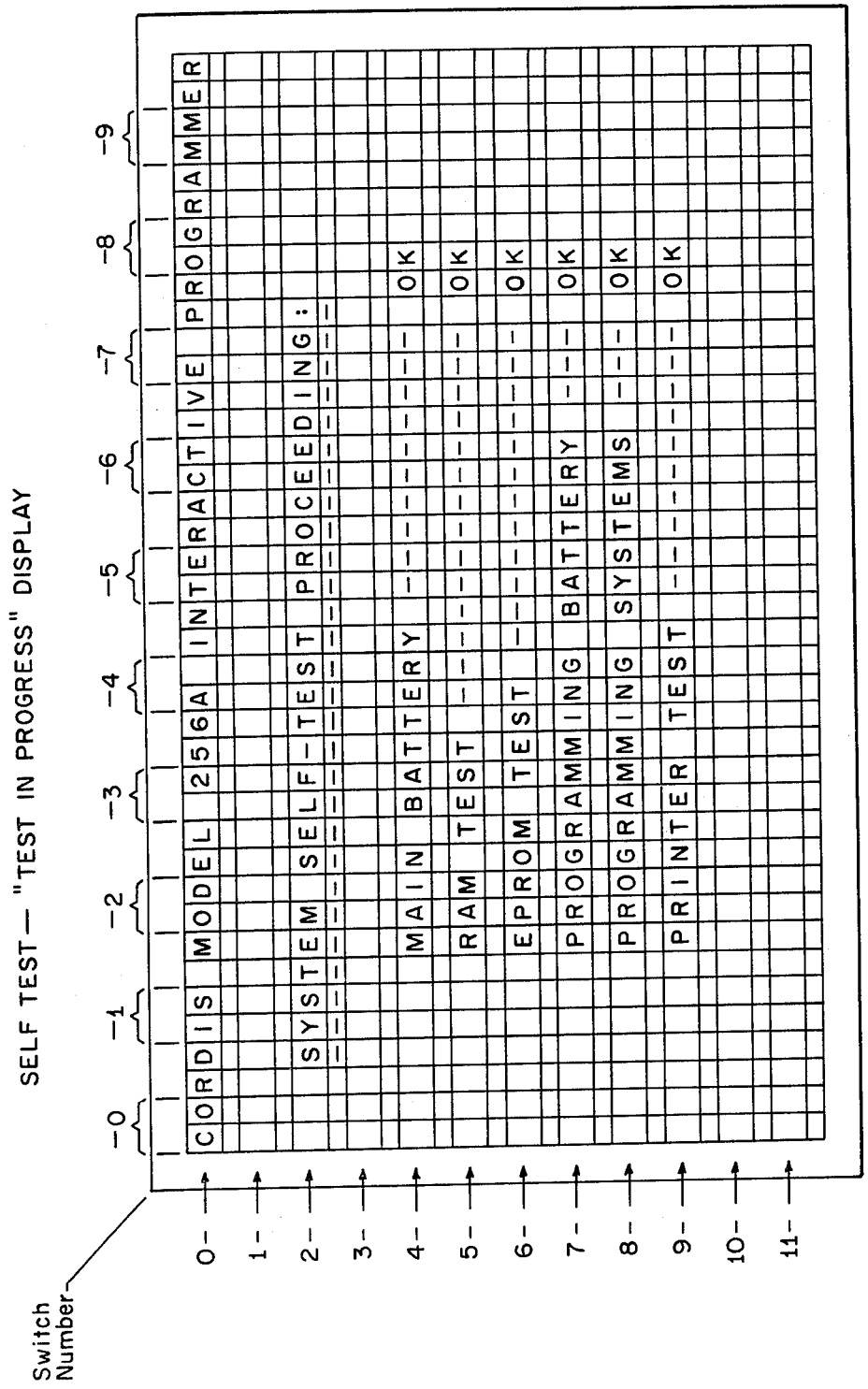
FIG. 15A  SELF TEST — "TEST IN PROGRESS" DISPLAY

SELF TEST — MAIN BATTERY MESSAGE #1

Message occurs when system on a-c power.
Message displayed for 3 seconds, then self-test sequence resumed.

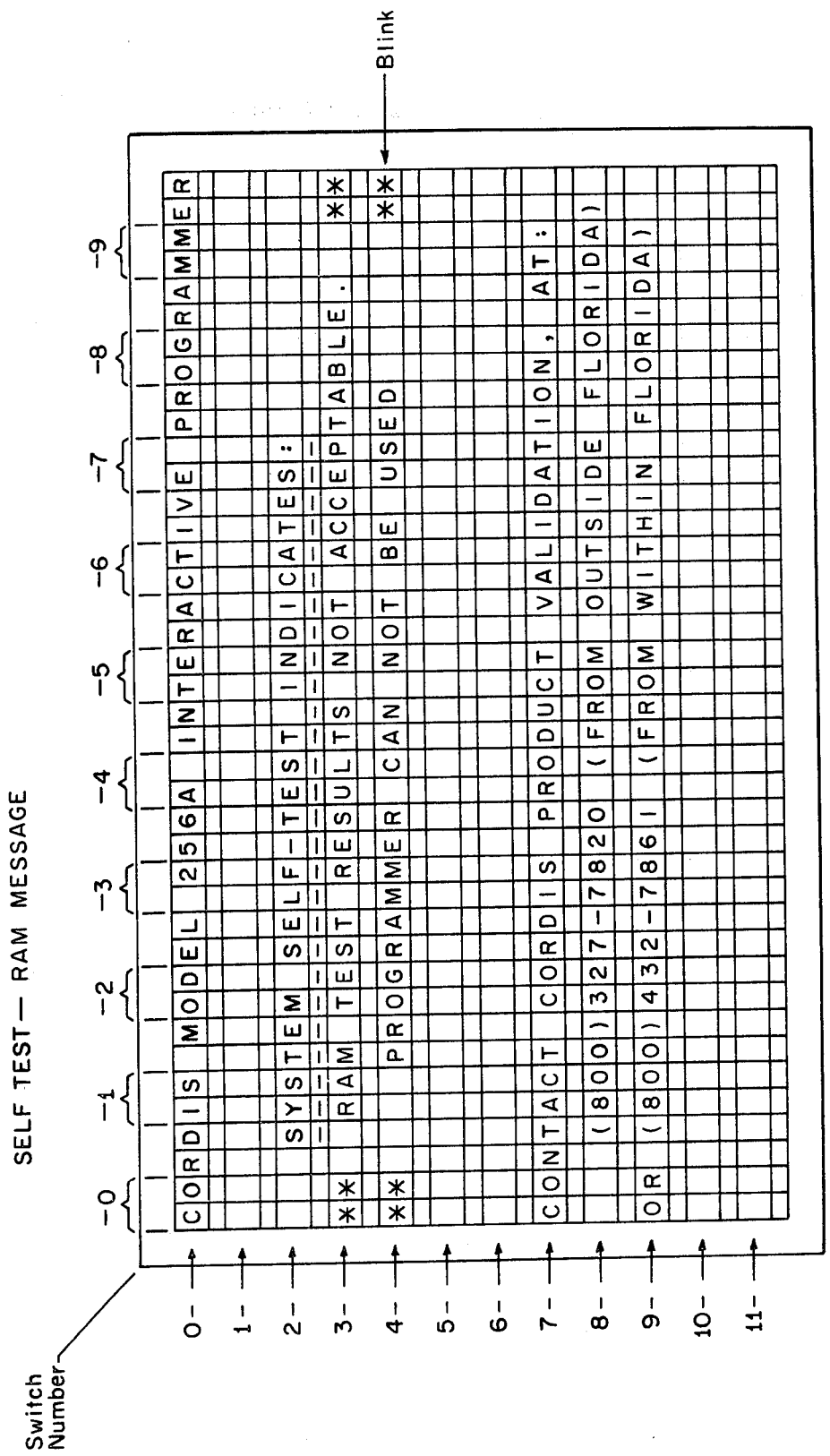
FIG. 15C  SELF TEST — RAM MESSAGE

SELF TEST—HEAD QUESTION

Console "BEEPS" for two seconds.
Message displayed until user presses appropriate input.

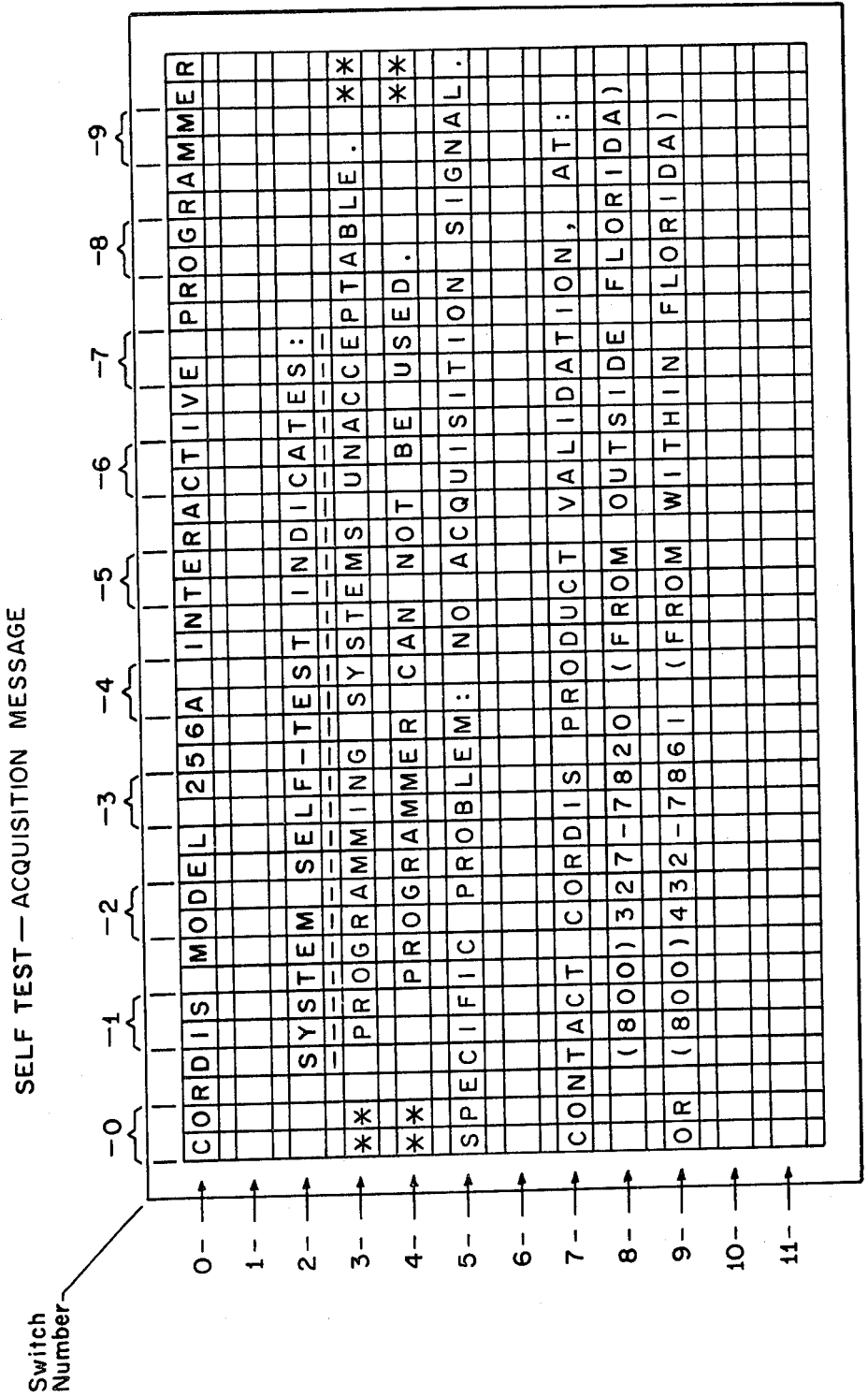
FIG. 15E SELF TEST—ACQUISITION MESSAGE
Console "BEEPS" for two seconds.
System stops at this point.

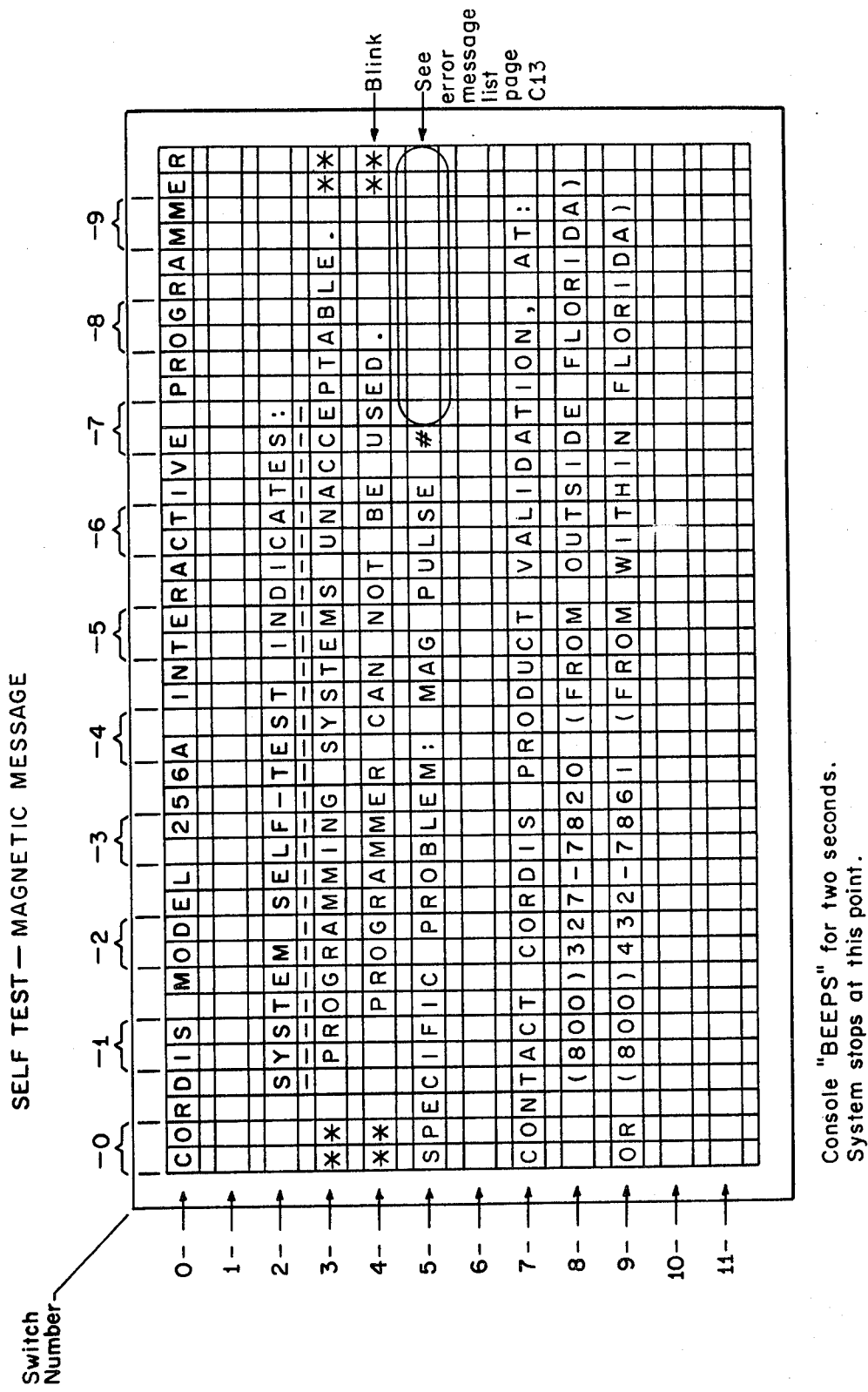
FIG. 15F SELF TEST — MAGNETIC MESSAGE

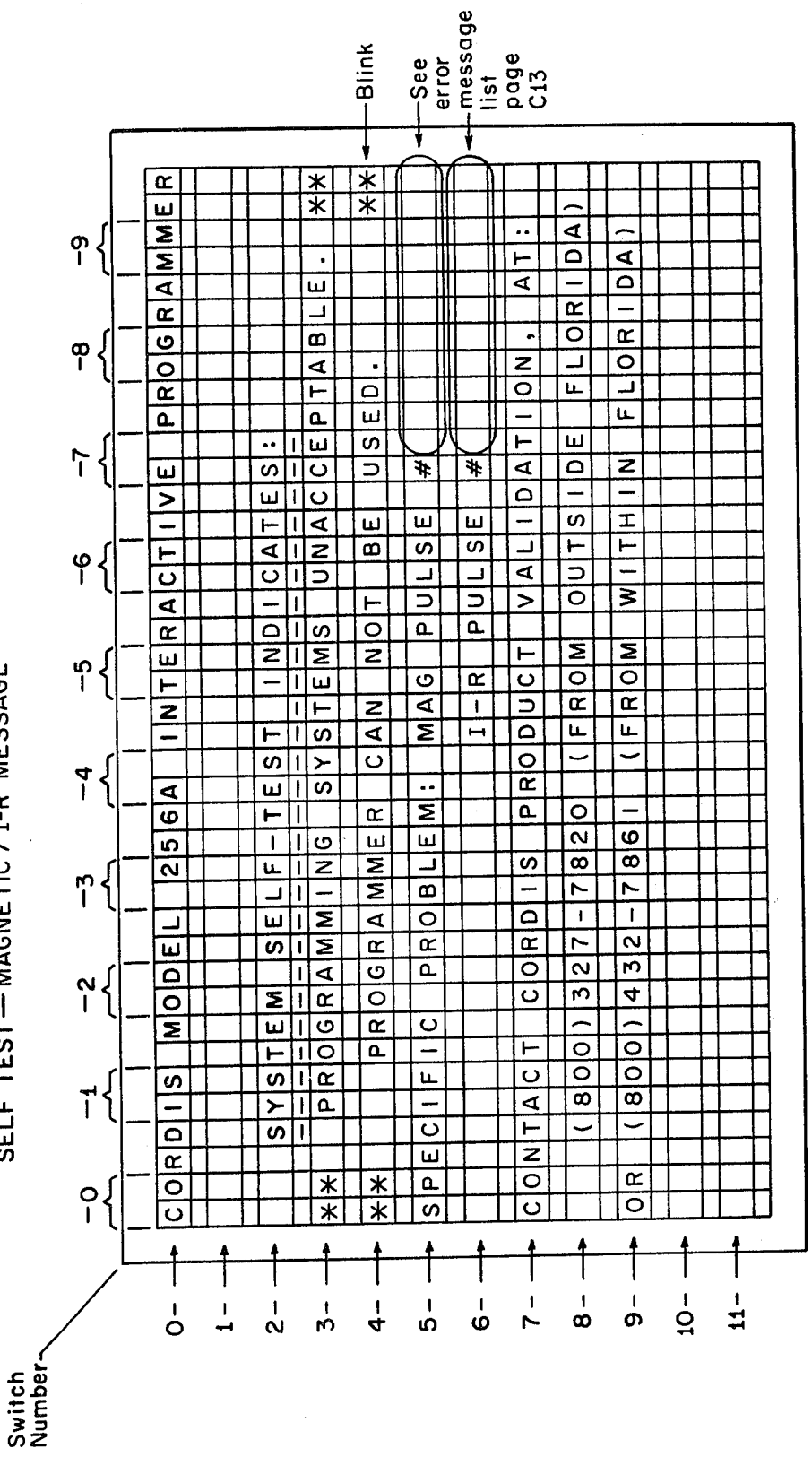
FIG. 15G  SELF TEST—MAGNETIC/I-R MESSAGE

SELF TEST — I/R MESSAGE

Step 1. Display after model number and electrode information (if necessary) are selected. Press targets at desired values.

```
MODEL  162D    OMNISTANICOR       ◆LIST MODELS
               RATE        OUTPUT      MODE

PROPOSED:       ---         ---         ---
_____

RATE  (PPM):         OUTPUT:        MODE:
◆60         ◆80       ◆2 MA      ◆SENSING
◆65         ◆90       ◆4 MA        (VVI)
◆70         ◆100      ◆6 MA      ◆ASYNCH
                      ◆9 MA        (VOO)
YOU  MUST  SPECIFY  A  VALUE  FOR  EACH  OF  THE
THREE  PARAMETERS  BEFORE  PROGRAMMING.
```

FIG. 16A

Step 2. Display after all parameter values are chosen. Press target at PROGRAM (bottom).

```
MODEL  162D    OMNISTANICOR       ◆LIST MODELS
               RATE        OUTPUT      MODE

PROPOSED:       65          4 MA      ASYNCH.
_____

RATE  (PPM):         OUTPUT:        MODE:
◆60         ◆80       ◆2 MA      ◆SENSING
◆65         ◆90       ◆4 MA        (VVI)
◆70         ◆100      ◆6 MA      ◆ASYNCH
                      ◆9 MA        (VOO)
_____
◆PROGRAM
```

FIG. 16B

Step 3. Program the implant by following the message or cancel programming command by pressing target at C A N C E L P E N D I N G   A C T I O N (display will return to Fig. 2).

```
MODEL 162D    OMNISTANICOR
               RATE      OUTPUT      MODE

PROPOSED:       65        4 MA       ASYNCH.
-----------------------------------------------
              ACTION: PENDING
            PROGRAM PROPOSED VALUES

PLACE PROGRAMMING HEAD OVER PACER
       PRESS AND RELEASE "ACTION" BUTTON
                      OR
              ◆CANCEL PENDING ACTION
```

FIG. 16C

Step 4. If no further changes are desired after programming, press the P R I N T target.

```
    MODEL 162D   OMNISTANICOR      ◆LIST MODELS
                  RATE      OUTPUT      MODE
    PRESENT:       65        4 MA      ASYNCH.
    PROPOSED:      65        4 MA      ASYNCH.
    ---------------------------------------------
      RATE (PPM):      OUTPUT:        MODE:
      ◆60    ◆80       ◆2 MA         ◆SENSING
      ◆65    ◆90       ◆4 MA           (VVI)
      ◆70    ◆100      ◆6 MA         ◆ASYNCH
                       ◆9 MA           (VOO)
    ---------------------------------------------
        ◆PROGRAM              ◆PRINT
```

FIG. 16D

Step 5. A typical printout (Model 162D shown). Attach this to the patient's records.

```
      CORDIS
  PROGRAMMING RECORD

DATE: 23 DEC 80
TIME:  3:54 PM

MODEL 162D

ELECTRODE LOCATION:
     VENTRICLE

PROGRAMMED VALUES:

RATE: 65  PPM
OUTPUT: 4 MA
MODE: ASYNCH.

PT. NAME:
- - - - - - - - -
PACER S/N:
- - - - - - - - -
PROG. BY:
- - - - - - - - -
PLACE:
- - - - - - - - -
DOCTOR:
- - - - - - - - -
REMARKS:
- - - - - - - - -

Step 1. Display after model number and electrode information (if necessary) are selected. Press target at the type of parameter desired from the left side.

```
┌─────────────────────────┬─────────────────────────┐
│ MODEL 336 MULTICOR      │     NEXT ACTION:        │
│   PROPOSED VALUES       │                         │
│ ◆RATE: -----------      │ PROGRAM:   PROPOSED     │
│ ◆OUTPUT: ---------      │          ◆ STANDARD     │
│ ◆SENSITIV: -------      │                         │
│ ◆MODE: -----------      │ DISPLAY :  PRESENT      │
│ ◆ANODE: ----------      │          ◆ PROPOSED     │
│                         │          ◆ STANDARD     │
│ ─────────────────────   │                         │
│ YOU MUST SPECIFY A      │                         │
│ VALUE FOR EACH OF       │    PRINT PRESENT        │
│ THE PARAMETERS          │                         │
│ BEFORE PROGRAMMING      │    ◆LIST MODELS         │
└─────────────────────────┴─────────────────────────┘
```

FIG. 18A

Step 2. The right side now displays the range of values available for the parameter type selected. Choose the value desired and then select another parameter from the left side of the screen. Repeat until values for all parameters are selected, then press the target at G O  T O  A C T I O N  L I S T  (bottom).

```
┌─────────────────────────┬─────────────────────────┐
│ MODEL 336 MULTICOR      │   SENSITIVITY (MV):     │
│   PROPOSED VALUES       │       ◆0.8              │
│ ◆RATE: 60 PPM           │       ◆1.5              │
│ ◆OUTPUT: 4 MA           │       ◆2.5              │
│ ◆SENSITIV: -------      │       ◆3.0              │
│ ◆MODE: -----------      │       ◆3.5              │
│ ◆ANODE: ----------      │       ◆4.0              │
│                         │       ◆5.0              │
│ ─────────────────────   │       ◆5.5              │
│ YOU MUST SPECIFY A      │                         │
│ VALUE FOR EACH OF       │                         │
│ THE PARAMETERS          │                         │
│ BEFORE PROGRAMMING.     │  ◆GO TO ACTION LIST     │
└─────────────────────────┴─────────────────────────┘
```

FIG. 18B

Step 3. Press target at PROGRAM: PROPOSED in the action list.

```
MODEL 336 MULTICOR    |   NEXT ACTION:
  PROPOSED VALUES     |
◆RATE: 60 PPM         |   PROGRAM:  ◆PROPOSED
◆OUTPUT: 4 MA         |             ◆STANDARD
◆SENSITIV: 2.5 MV     |
◆MODE  SENSING-VVI    |   DISPLAY : PRESENT
◆ANODE: CASE          |             ◆PROPOSED
----------------------|             ◆STANDARD
                      |
                      |   PRINT PRESENT
                      |
                      |   ◆LIST MODELS
```

FIG. 18C

Step 4. Program the implant by following the message or cancel programming command by pressing the target at CANCEL ACTION (bottom).

```
MODEL 336 MULTICOR    |   ACTION PENDING
  PROPOSED VALUES     |
RATE: 60 PPM          |   PROGRAM PROPOSED.
OUTPUT: 4 MA          |
SENSITIV: 2.5 MV      |        PLACE
MODE: SENSING-VVI     |   PROGRAMMING HEAD
ANODE: CASE           |      OVER PACER
----------------------|   PRESS AND RELEASE
                      |    "ACTION" BUTTON
                      |
                      |          OR
                      |   ◆CANCEL ACTION
```

FIG. 18D

Step 5. If no further changes are desired after programming, press the PRINT PRESENT target.

```
MODEL 336 MULTICOR    |   NEXT ACTION:
   PRESENT VALUES     |
◆RATE: 60 PPM         |   PROGRAM:  ◆PROPOSED
◆OUTPUT: 4 MA         |             ◆STANDARD
◆SENSITIV: 2.5 MV     |
◆MODE: SENSING-VVI    |   DISPLAY : ◆PRESENT
◆ANODE: CASE          |             ◆PROPOSED
----------------------|             ◆STANDARD
                      |
                      |   ◆PRINT PRESENT
                      |
                      |   ◆LIST MODELS
```

FIG. 18E

Step 6. A typical printout for these implants (Model 336 Multicor Gamma shown). Attach this to the patient's records.

```
        CORDIS
   PROGRAMMING RECORD

DATE: 23 DEC 80
   TIME:  3:49 PM

MODEL 336

ELECTRODE:
       TYPE - UNIPOLAR
   LOCATION - VENTRICLE

PROGRAMMED VALUES:

RATE: 60  PPM
   OUTPUT: 4 MA
   SENSITIV.: 2.5 MV
   MODE: SENSING-VVI
   ANODE: CASE

PT. NAME:
   _ _ _ _ _ _ _ _ _ _

PACER S/N:
   _ _ _ _ _ _ _ _ _ _

PROG. BY:
   _ _ _ _ _ _ _ _ _ _

PLACE:
   _ _ _ _ _ _ _ _ _ _

DOCTOR:
   _ _ _ _ _ _ _ _ _ _

REMARKS:
   _ _ _ _ _ _ _ _ _ _

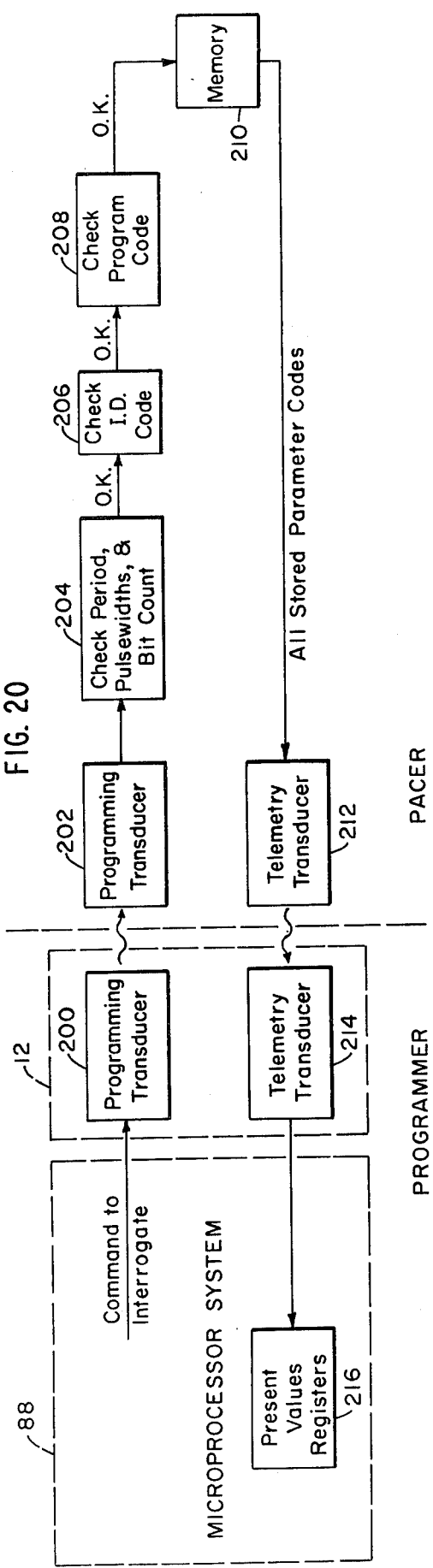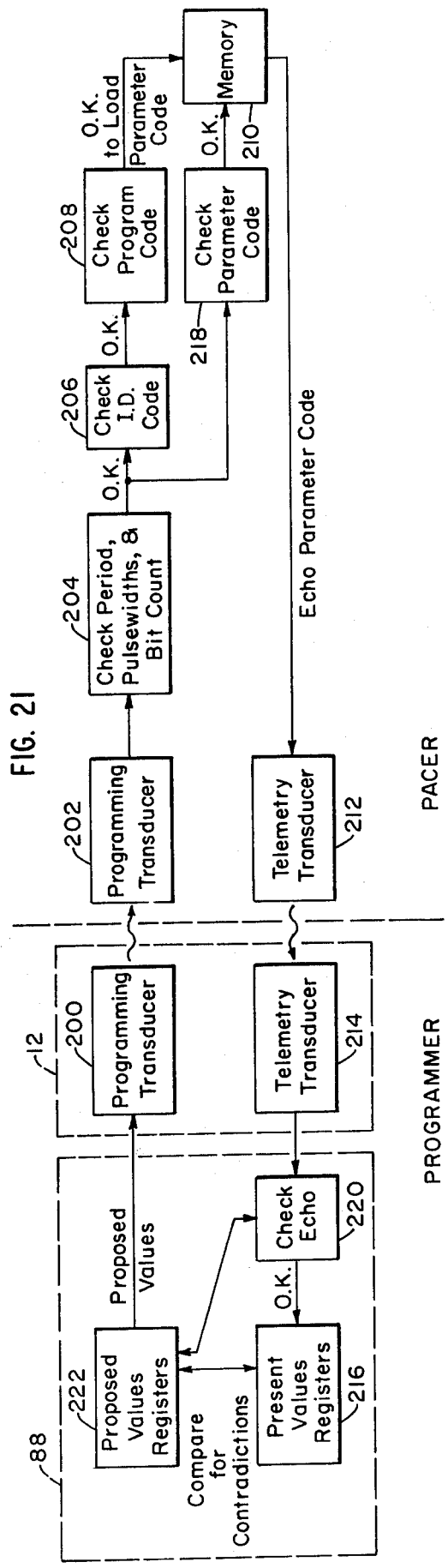

INTERACTIVE PROGRAMMER FOR BIOMEDICAL IMPLANTABLE DEVICES

CROSS REFERENCE TO RELATED APPLICATIONS

This application is related generally to the following U.S. applications, each of which is assigned to the assignee of the present application and incorporated by reference herein in its entirety:

| Serial No. | Filed | Title | Inventor(s) |
|---|---|---|---|
| 153,093 | 5/27/80 | Implant Telemetry System | Slocum et al. |
| 195,665 | 10/9/80 | Implantable Externally Programmable Microprocessor Controlled Tissue Stimulator | Lesnick |
| 207,003 | 11/14/80 | Multi-Mode Microprocessor-Based Programmable Cardiac Pacer | Leckrone et al. |
| 239,467 | 3/2/81 | Cardiac Pacer With Improved Battery System, Output Circuitry, and Emergency Operation | Saulson et al. |
| 239,468 | 3/2/81 | Cardiac Pacer With Improved Battery System, Output Circuitry, and Emergency Operation | Saulson et al. |

BACKGROUND OF THE INVENTION

The invention relates generally to the field of programmable biomedical implantable devices and more particularly to external programmers for implanted cardiac pacers and neural stimulators.

A cardiac pacer is a life-sustaining therapeutic device which cooperates with the patient's heart by causing it to beat in a natural rhythm when the heart may othewise fail to provide adequate blood circulation. Commercially practicable cardiac pacers are powered by self-contained batteries and fully implanted in hermetically sealed or encapsulated containers in the patient's body, for example, in the shoulder region just beneath the skin. Electrical conductors called pacer leads run from the implant through an opening beneath the skin in a nearby vein and extend through the vein to the heart. The lead terminates in an electrode which contacts the interior wall of the heart muscle. Electrical stimulation pulses are generated by the cardiac pacer and applied via the pacer lead to the cardiac muscle to stimulate contraction, particularly when spontaneous natural heart action is absent. Along with the batteries, the implanted pacer includes electronic circuitry for generating the stimulation pulses. The pulses which are applied to the heart muscle have two fundamental variable characteristics or parameters: pulse intensity and pulse timing. Pulse intensity normally refers to the amplitude (pulse height) of the electrical current flowing to the heart muscle via the pacer lead during the pulse. Pulse timing refers to the duration (pulse width) of the pulse as well as to the time interval between pulses (interpulse period), which is related to the pulse rate, e.g., 70 beats per minute.

In early pacemakers the pulse parameters were fixed, established during manufacture. In 1972 the first digital programmable pacemaker, the Cordis Omnicor, was introduced to the market. The term "programmable" in this context means the ability to alter parameter values in the implant noninvasively from outside the body by transferring parameter data from an external programmer to the implant. See, for example, U.S. Pat. No. 3,805,796 to Terry et al. Digital pacing generally refers to the use of a digital counting chain driven by a high frequency oscillator to determine all the timing intervals. See, for example, U.S. Pat. No. 3,557,796 to Keller et al. The advantages of programmability once obtained were readily apparent. Since most cardiac patients are in a continually changing, and for older patients, usually declining state of health, the optimum pacer parameters must be changed frequently during the patient's lifetime. Without programmability such changes involved surgery or invasive techniques which ran significantly increased risk of infection due to the presence of the foreign body in the patient. This risk is eliminated by programmability. Secondly, a manufacturer does not have to proliferate an inventory of models of pacers which vary only in parameter values. Today these advantages are such that nearly all pacemakers are, and many argue all should be, programmable.

Nevertheless, programmability has not given rise to a universal pacer, i.e. a single model. Instead, with the continual march of technology and medical science, as well as the need for pacers which operate in limited pacing models such as ventricular inhibited pacing and AV synchronous or AV sequential pacing, a successful pacer manufacturer must contend with a growing host of pacers all implanted in living human patients and many programmable in different ways. The future definitely holds in store implanted pacers with telemetry for data communication with the outside world. New pacing modes, diagnostic techniques and temporary pacing treatments will also undoubtedly be discovered.

The challenge is to develop a programmer which is versatile enough to program all of these pacer products safely noninvasively and with a procedure as straightforward as the functional requirements.

SUMMARY OF THE INVENTION

A computer-controlled programmer having a user-interactive display is designed to control the parameters of a wide variety of implantable devices, particularly cardiac pacers and neutral stimulators, with different programming requirements. During programming, screen messages prompt the user to perform required actions by pressing lighted targets on the display screen. The programmer includes a console and a lightweight cable-connected programming head. When the console is turned on, a self test routine automatically tests the batteries, memory banks and communications system. For the communications test, the programmer employs a self-contained telemetry system which mimics the response of an implant. Standard values can be rapidly programmed for any of the selected type of implants (cardiac or neutral) at any time during the programming procedure by means of either a "standard" button located on the programming head or a switch on the console. The programmer produces an intermittent audio tone when the power is turned on and when standard values are selected. A steady tone accompanies the transmission of the programming pulses to the implant. A pulsating tone at the end of transmission or during self test indicates a possible problem. The console's display provides instructions for correcting detected problems. The programmer automatically changes programming options in response to certain information received from an implant with telemetry as well as in response to selection of certain modes and lead configurations. The programmer software is designed to limit access to certain ranges of values of parameters and certain parameters themselves, which require the attendance of an authorized physician. The physician gains acces to these less routine programming functions by entering a predetermined numerical code via a "combination lock" on the front panel of the console. With certain implants having data telemetry, the programmer software is designed to confirm programming by comparing the originally transmitted programming data to an automatic echo of the programming data received by the implant.

BRIEF DESCRIPTION OF THE DRAWING

FIGS. 15A–15H are pictorial representations of the self test display formats which appear on the screen of FIG. 1 following turn on.

FIGS. 16A–16D are pictorial representations of the sequence of displays for programming the Omni-Stanicor Model No. 162D.

FIG. 17 is a sample printout of the interactive programmer of FIG. 1 recording typical programming of a Model 162D.

FIGS. 18A–18E are pictorial representations of a typical sequence of display formats for programming the Model No. 336 Multicor-Gamma pacer.

FIG. 19 is a sample printout for Model No. 336.

FIG. 20 is a functional block diagram illustrating the preferred system for interrogating an implant with telemetry.

FIG. 21 is a functional block diagram illustrating the preferred system for programming an implant with telemetry.

DESCRIPTION OF THE PREFERRED EMBODIMENT

The programmer described below is an external instrument capable of noninvasively controlling the parameter settings (i.e., programming) for implantable pulse generators manufactured by Cordis Corp., the assignee of the present application. Unless otherwise indicated, the implanted pulse generators themselves are not a part of this disclosure. In fact, the assignee has a wide variety of programmable pulse generators presently on the market or in use. Up until recently all of these units have been designed to be programmed by a string of magnetic pulses which are counted by the implant. The number of pulses in the string determines the parameter and selected parameter value in this type of implant. The Omnicor and Sequicor pacers and the 900 series neural stimulators are reprogrammed in response to the length of one or more strings of magnetic pulses at a single rate while the recently introduced Multicor pacers respond to the length of strings of magnetic pulses of differing rates. Implants which are in the process of being introduced to the marketplace respond to binary information expressed as a string of pulse width modulated magnetic or infrared pulses. Moreover, the programmer is designed to receive myriametric telemetry of the type described in U.S. Pat. No. 4,361,153 and copending application Ser. No. 195,665.

Figure 1A:
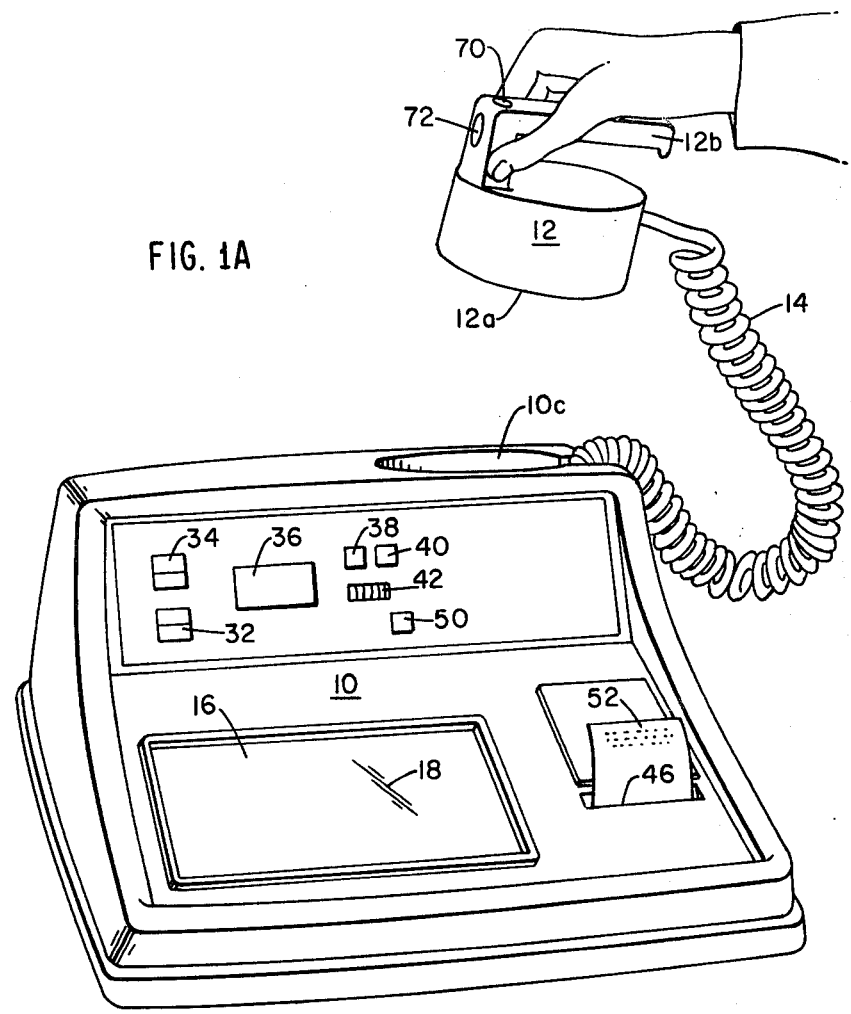
FIG. 1 is a perspective view of a preferred embodiment of the interactive programmer according to the invention.
Figure 1B:
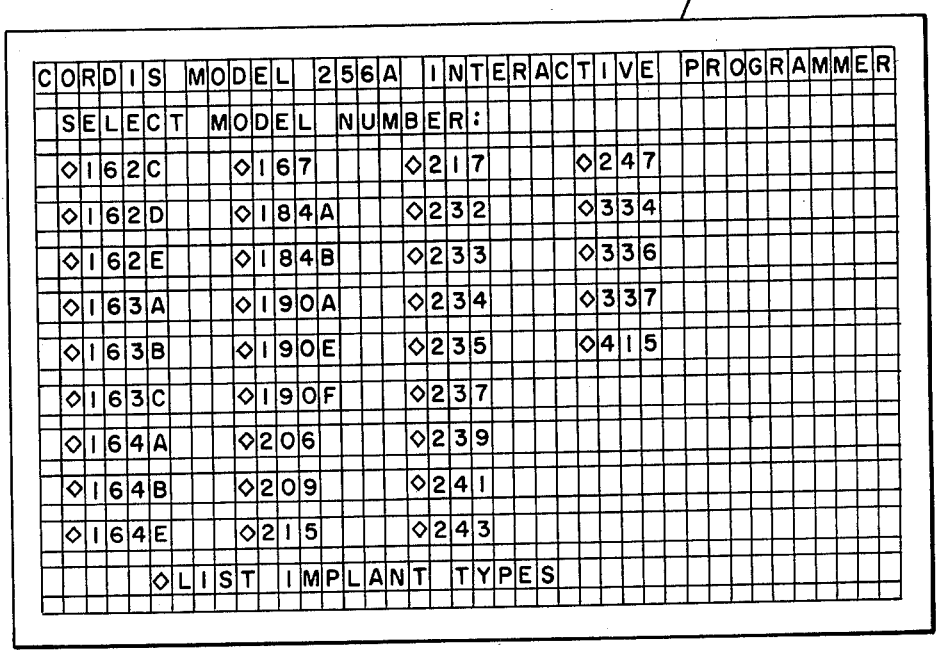
Figure 2:
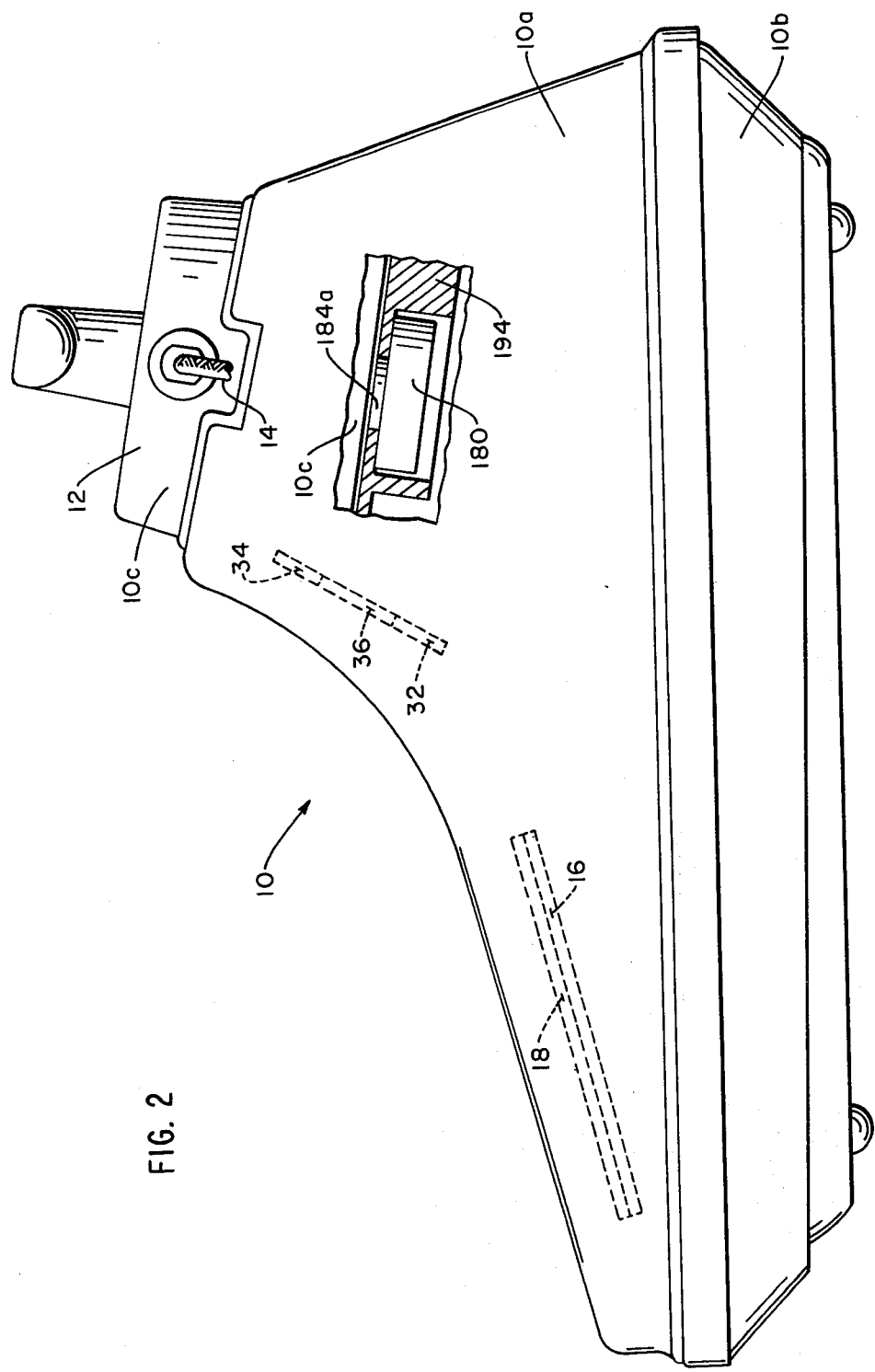
FIG. 2 is a side view of the interactive programmer of FIG. 1 in elevation with a portion broken away to reveal the location of the self test module.

As shown in FIG. 1, the interactive programmer consists of two units: a main tabletop console 10 and a lightweight handheld programming head 12 interconnected with the console by cable 14. The programming head 12 is described in detail in U.S. Pat. No. 4,361,153. The console 10 includes a rectangular outer case of injection molded high impact polystyrene approximately 13 inches wide by 19 inches deep with a sloping upper face approximately 2 inches high in front and 10¼ inches high at the back. The console case consists of two halves 10a and 10b as shown in FIG. 2, which fit together in a clamshell arrangement hinged at the rear with a sealing gasket (not shown) at the junction. The front of the console 10 includes displays and touch switches for interacting with the operator as well as a thermal printer for recording the programming operation. A versatile alpha numeric display 16 is mounted in the lower portion of the front panel. Preferably, the display is in the form of a gas discharge display matrix presenting twelve lines of forty characters each. The display includes a standard sixty-four character ASCII character set in a 5×7 element array (plus five additional elements for underlining) modified to include six custom characters, namely a filled in diamond for the pushbutton targets, the Greek letters delta, omega and mu and a full height vertical line as well as a 5×7 cross for graphic use in separating the screen into sections. The display of choice is presently an IEE Argus 480 gas discharge display which presents bright red characters against dark background. The Argus display requires a six bit parallel input for the character, plus two bits for underlining, blinking and half bright features. In addition, a switchable logic line allows the screen to be turned off to conserve power without loss of memory contents of the screen.

Figure 3:
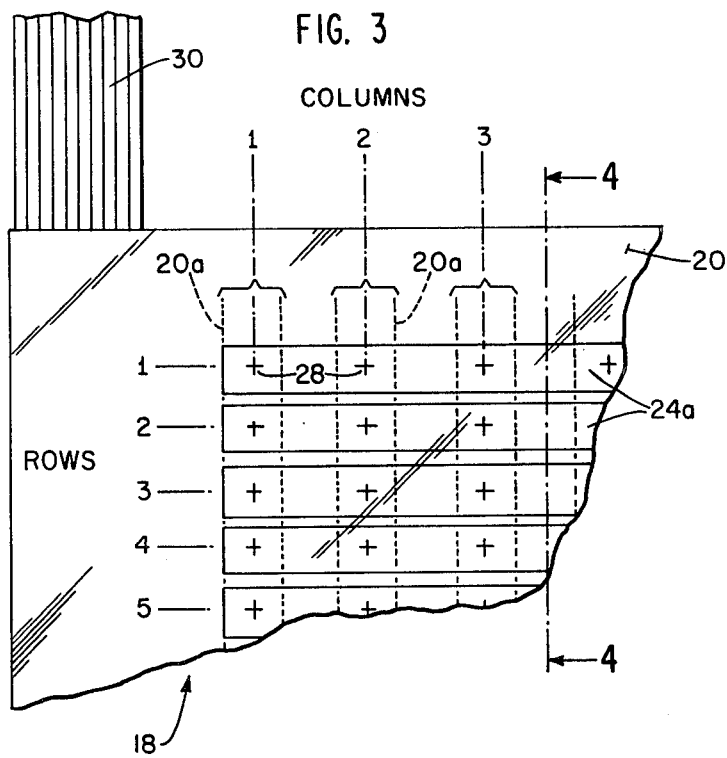
FIG. 3 is a plan view, as seen by the operator, of the transparent switch matrix overlay for the display in the programmer of FIG. 1.
Figure 4:
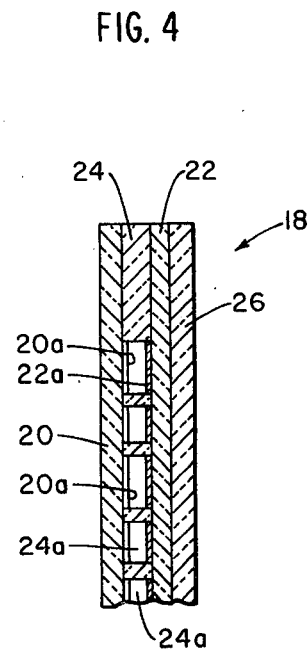
FIG. 4 is an exaggerated sectional view taken along lines 4—4 of FIG. 3 illustrating the construction of the overlay.

Over the rectangular matrix of the alpha numeric display 16 there is a transparent, mechanical, touch sensitive switch matrix overlay 18. The display 16 can be read through the switch overlay 18. As shown in FIG. 4, the overlay 18 itself is comprised of a plurality of flexible transparent sheets. The switch assembly includes a pair of parallel substrates 20 and 22 and a separator 24. One of the substrates 20 has a plurality of parallel conductive paths deposited on the inner surface thereof and arranged in the form of spaced parallel columns 20a as shown in FIGS. 3 and 4. The separator 24 includes a plurality of spaced parallel laterally extending rectangular apertures 24a. The other substrate 22 includes a plurality of spaced parallel conductive paths 22a deposited on the inner surface thereof and approximately coextensive with the adjacent separator apertures 24a. An optional filter sheet 26 is mounted over the upper one of the substrates to complete the overlay switch matrix. A typical switch is operated by pressing the overlay assembly at the intersection of a row path 22a with a column path 20a for example at location 28. The conductive paths can make contact through the apertures 24a of FIG. 3. In the preferred design, ten conductive columns 20a are arranged in conjunction with twelve conductive rows 22a to form a matrix of one-hundred and twenty switches over the twelve line alpha numeric display. The switch positions 28 are preferably four display characters apart and cover two characters each. Thus for each line the switches cover characters 1 and 2, 5 and 6 9 and 10 and so on up to characters 37 and 38. When a particular one of the switches is pressed, the decoding logic in the console 10 which periodically polls the switch matrix, provides a ready signal and an 8 bit data word identifying the switch that was pressed. The overlay 18 produces outputs for the ten columns and twelve rows on twenty-two line ribbon conductor 30.

Figure 7:
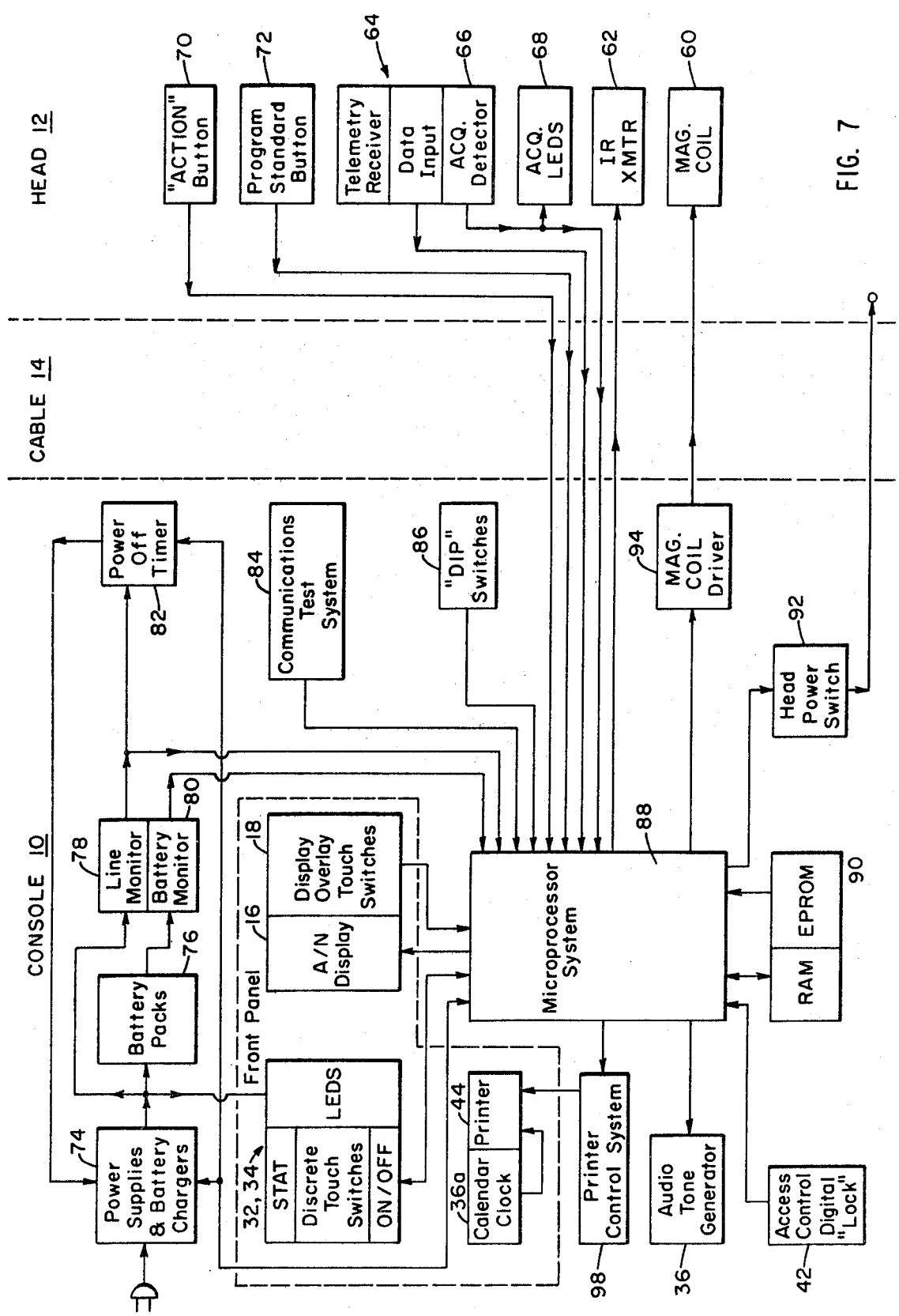
FIG. 7 is a functional block diagram of the electronics for the interactive programmer of FIG. 1.

In addition to the alpha numeric display 16, the front of the console 10 includes bistable touch switches 32 and 34 illuminated with respective light emitting diodes (LED's). Switch 32 is an on/off charge button which when pressed and released turns the programmer on. The word "ON" appears in the top half of the button and the programmer "beeps" once via an audible tone generator 36 (FIG. 7). When the button is pressed and released again, the programmer is turned off and the word "CHARGE" appears if the programmer is plugged into a wall outlet at the time. Switch 34 is the "STAT SET" button for programming standard values for pacers and for turning neural stimulators off. After the interactive programmer has been turned on, and the implant type has been selected if required, the words "STAT SET" appear in the button. If the user pushes the button, the programmer "beeps". The stat set values for the pacer model will appear on the display screen 16 after which they can be programmed into the pacer. A liquid crystal display 36 shows the time of day unless data and year are being set. Switches 38 and 40 are mode and increment buttons used to reset the calendar clock. Combination lock 42 is used to control the level of access to the interactive programmer. The combination lock consists of two sets of thumbwheel switches, one set (not shown) is concealed behind a locked door. The interactive programmer is designed so that when the user attempts to program a particular implant or a particularly sensitive parameter, the system will check to see if access is restricted. If it is, the system will check to see if the correct combination has been entered on combination lock 42. If it has been entered, the interactive programmer will be in the full access mode; if not, it will be in the "limited access" mode.

The console 10 is also equipped with a printer 44. The printer is preferably a Texas Instruments EPN 9120, twenty column thermal printer employing 2½ inch wide paper which exits through slot 46 on the front of the console. A printer control system 48 (FIG. 7) causes the printer to print out the programmed parameters, Model No., date and time. Date and time are provided by a four-year calendar clock chip 36a powered by an independent battery. Button 50 in the console advances the printout paper which can be restocked via the access door 52 on the front of the console 10.

Programming head 12 has a flat circular bottom portion 12a which the operator positions over the site of the implant for programming. The programming head 12 (FIG. 7) contains a magnetic coil 60, an infrared transmitter 62 and a reflected signal telemetry receiving system 64, described in detail in U.S. Pat. No. 4,361,153. The telemetry receiver 64 is also used even in non-telemetry implants to produce an acquisition signal from an acquisition detector 66 which drives an acquisition lead or leads 68. Preferably a pair of LED's 68 are used, a yellow and a green, mounted in the upper surface of the cylindrical body of the programming head. Together, these lights form the "acquisition" indicator which, when lit, inform the user that the programming head is within working distance of the implant. The thresholds for the yellow and green lights are set differentially so that the yellow light comes on first (e.g. 1½ inches) followed by the green light (e.g., 1 inch) as the programming head approaches the implant. The handle 12b of the programming head 12 is equipped with an action button 70 located at the top of the handle "under the user's thumb" (FIGS. 1 and 7). The action button 70 is pushed and released to produce a programming transmission. In the front of the upright portion of the handle 12b a STAT SET button 72 is provided for emergency programming of standard parameter values and modes considered safe for most patients without having to leave the patient to return to the console. Details of preferred circuitry for the programming head are disclosed in U.S. Pat. No. 4,361,153.

Power is provided to the console 10 and head 12 via power supplies and battery chargers 74. Battery packs 76 include a main or system battery and a programming battery. The programming battery preferably consists of fourteen sealed rechargeable Ni-Cd fet-A cells in series providing 16.8 volts with a 0.7 ampere hour capacity. The programming battery provides power for the programming output and printer. The system battery comprises preferably ten sealed rechargeable Ni-Cd size ⅓A cells in series providing 12 volts with a 0.15 ampere hour capacity, for use during temporary power losses by providing up to thirty seconds of operation to avoid misprogrammings. All operations, such as interaction with the display during selection of parameter values, are powered by line current, except for programming. The batteries are continuously charged during on line operation. The battery charger for the programming battery is separate from the battery charger for the backup battery. A line monitor and battery monitors 78 and 80 continuously advise the console electronics of any unacceptable power drop. A power-off timer 82 is used during the battery self test mode described below. The console 10 also includes a separate communications test system 84 for checking the telemetry receiver 64, IR transmitter 62 and mag coil 60 of the programming head 12. DIP switches 86 enable the console to be preset to accommodate either neural or cardiac pacer implants or to bypass the access control digital lock 42. The console is operated via a single microprocessor system 88 with associated memory 90. Power for the programming head is provided via the head power switch 92 controlled by the microprocessor system and the high current required for the magnetic coil 60 is provided separately via a mag coil lever 94 located in the console 10.

The electronic circuitry of the console 10 is identified in FIGS. 8-13 with the exception of the printer control system comprising a separate microcomputer system. The overall organization of the electronics of console 10 can be appreciated from FIG. 8. The main power board 100, transformer 102, heat sink mounted components 104, "mod" board power supply 106, and 12 volt and 18 volt battery packs 108 and 110 supply the required voltages and currents for operating the remainder of the electronics, for example, to power the display 16 and overlay switches 18. The console switch board 112 carries the on/off and STAT SET lighted panel switches 32 and 34. "LINE ON" is an input to the console switchboard 112 originating from the main power board 100 which causes the charge indicator light to be illuminated on the on/off switch when the unit is plugged into a source of line current. The Std. LED K input to the console switchboard 112 causes the STET SET switch to be illuminated after selecting neural or cardiac pacer implants.

The operating system electronics are provided on a series of printed circuit cards of the RCA Microboard configuration carried in standard CDS card cage. The circuit boards are interconnected by a backplane connector 114. The heart of the system is the CPU board 116 which comprises a standard commercially available RCA Microboard CDP 18S603 diagrammed generally in FIG. 9. The single chip RCA CDP 1802 microprocessor 118 is driven by a 2 MHz crystal 120 and is interfaced with one kilobyte of RAM 122 by means of an address latch and decode circuit 124. The control, data and address busses of the microboard bus interface system are connected to the microboard universal backplane connector P1 which have the following standard designations within the RCA 1800 microprocessor system.

TABLE I

| Pin | Signal | Pin | Signal |
|-----|--------|-----|--------|
| A | TPA-P | 1 | DMAI-N |
| B | TPB-P | 2 | DMAO-N |
| C | DBO-P | 3 | RNU-P |
| D | DBI-P | 4 | INT-N |
| E | DB2-P | 5 | MRD-N |
| F | DB3-P | 6 | Q-P |
| H | DB4-P | 7 | SCO-P |
| J | DB5-P | 8 | SCI-P |
| K | DB6-P | 9 | CLEAR-N |
| L | DB7-P | 10 | WAIT-N |
| M | AO-P | 11 | −5V/−15V |
| N | AI-P | 12 | SPARE |
| P | A2-P | 13 | CLOCK OUT |
| R | A3-P | 14 | NO-P |
| S | A4-P | 15 | N1-P |
| T | A5-P | 16 | N2-P |
| U | A6-P | 17 | EF1-N |
| V | A7-P | 18 | EF2-N |
| W | MRW-N | 19 | EF3-N |
| X | EF4-N | 20 | +12V/+15V |
| Y | +5V | 21 | +5V |
| Z | GND | 22 | GND |

The letters "P" and "N" in the foregong table designate positive or negative signal level. The serial and parallel I/O interface circuitry and ROM available on the CPU board 116 are not used. All of the read only memory is furnished on a separate standard memory board, namely the RCA Microboard 32/64 kilobyte EPROM/ROM/RAM CDP18S626 which is diagrammed generally in FIG. 10. Ten of the sixteen memory sockets are used for INTEL 7732 EPROM's to provide a 40 kilobyte memory matrix 128 connected to the backplane connector by way of an address latch 130, address decoder 132, signal conditioning circuit 134, inhibit logic circuit 136 and bidirectional bus drivers 138. The EPROM addresses used run in hex code from location 000 through 9FFF. RAM locations on the microboard 116 employed in this system start at location F000 and extend to location F3FF. Memory board 126 contains the firmware program instructions for operating the CPU board 116. The microcomputer system is interfaced with the beeper 140 on the console switchboard 112, the alpha numeric display 16, the overlay switches 18, the limited access switchboard 42, the DIPswitch option board 86 and the communications test system 84 (FIG. 7) by means of a digital I/O board 142 which also carries the electronics for the communications test system. The I/O portion of board 142, also connected to the backplane, is shown in detail in FIG. 11. In FIG. 11, devices U411 through U415 are all identical eight bit I/O ports (RCA CDP1852). U409 is an n-bit decoder (CDP 1853). Devices U403 are a dual flipflop interconnected as shown in FIG. 11 with U404 which is a shift register which drives decoder/multiplexer arrangement U402 and U401 (CD4515 and CD4067 respectively) to interrogate the overlay switches. In FIG. 11, connections to the computer backplane are designated by BP(5) for pin 5 of connector P1 of the universal microboard connector. The connections to th analog card edge pseudo backplane connector are designated as, for example, (P)BP. That is, if the designation BP follows rather than precedes the pin designation, it refers to the analog card edge rather than the microcomputer backplane. The architecture of the 1802 microprocessor is arranged to provide access to seven input devices and seven output devices. The assembly language instruction OUT 1, for example, places the memory byte addressed by a particular register on the data bus. The three lower order bits of N are simultaneously sent from the CPU to the I/O system. In FIG. 11, this is accomplished in device U409. The N lines may be decoded with MRD-bar to select or control up to seven output devices. In a similar manner, the instruction INP 1 replaces memory byte addressed by the same register with an input byte. Similarly the N lines are decoded with MRD bar to select or control the seven possible input devices. The microprocessor also is furnished with four external flages EF1 through EF4 and a serial data output port Q. All of these various I/O control modalities are used in the interactive programmer.

The input-output hardware of the programmer shown in FIG. 11 services three classes of I/O functions. The first class of functions, "systems support", monitors line and battery voltages and enables the initial battery test. The second class of functions, "operator interface", runs the alpha numeric display, beeper, printer, lights for the front panel discrete switches 32, 34. In addition, operator interface includes responding to the following switches: display overlay switch matrix, panel switches, programming head switches, parameter access control and dip switch options. The third class functions relate to "programming-telemetry" interface, i.e. communications between the interactive programmer and the implant. These functions include generating the programming signals and enabling and receiving telemetry signals.

In the following table, the I/O ports are listed by functional classification. Each of the seven input or output ports accesses a full byte of data. However, in most of the cases which appear below only one bit of the accessed byte, for example, the least significant bit 0 of port INP 2, is used for a particular function.

TABLE II

SYSTEM SUPPORT

| PORT | BIT | FUNCTION |
|---|---|---|
| INP 2 | 0 | System Battery Monitor - high = weak |
| INP 2 | 1 | Telemetry Battery Monitor - high = weak |
| INP 2 | 6 | AC Line Monitor - high = AC on |
| OUT 4 | 2 | System Battery Check/Timer Reset - high = test/reset |

OPERATOR INTERFACE

| PORT | BIT | FUNCTION |
|---|---|---|
| EF | 1 | Display Switch Keypress - low = keypress |
| EF | 2 | Stat Set Head - low = press |
| EF | 3 | Action Button - low = press |
| INP 2 | 3 | Printer Busy - high = busy |
| INP 2 | 4 | Display Ready - high = ready |
| INP 2 | 5 | Parameter Access Control - low = full access |
| INP 2 | 7 | Stat Set Console - low = press |
| INP 3 | 0-7 | Printer-Clock Communication Port |
| INP 7 | 0-7 | Display Switch Decoder - Row, Col |

| DIP SWITCHES | SWITCH # | ON POSITION | OFF POSITION |
|---|---|---|---|
| INP 6 | 0 | 7 | By-pass IR Self-Test | Perform self test |
| | 1 | 8 | By-pass magnetic self test | Perform self test |
| | 2 | 1 | Implant Preference | No preference |
| | 3 | 2 | Neural Preference | Cardiac preference |
| | 4 | 3 | Beeper Disabled | Normal Operation |
| | 5 | 4 | Not Used | |
| | 6 | 5 | Not Used | |
| | 7 | 6 | By-pass printer self test | Perform self test |

| PORT | BIT | FUNCTION |
|---|---|---|
| OUT 2 | 6 | Clear display - high = clear |
| OUT 2 | 7 | Stat Set Backlight - high = lit |
| OUT 3 | 0-7 | Printer - high = data |
| OUT 4 | 1 | Beeper - high = beep |
| OUT 5 | 0-7 | Display - high = data |

PROGRAMMING-TELEMETRY INTERFACE

| PORT | BIT | FUNCTION |
|---|---|---|
| EF | 4 | Telemetry Data - low = data |
| INP 2 | 2 | Acquisition - low = acquisition |
| Q | | Programming Output - high = data |
| OUT 2 | 0 | IR Multiplexer - high = IR |
| | 1 | MAG Multiplexer - high = MAG |
| | 2 | Drive Enable - high = enabled |
| | 3 | Telemetry Enable 1 - high - enabled |
| | 4 | Telemetry Enable 2 - high = enabled |
| | 5 | Acquisition Latch - low = latch |
| OUT 4 | 0 | Head Power - high = on |

For convenience in correlating the I/O ports in FIG. 11 with Table II, the I/O ports are listed below in numerical order in Table III.

TABLE III

| PORT | BIT | FUNCTION |
|---|---|---|
| EF | 1 | Keypress |
| EF | 2 | Stat Set Head |
| EF | 3 | Action Button |
| EF | 4 | Telemetry Data |
| INP 2 | 0 | System Battery Monitor |
| | 1 | Telemetry Battery Monitor |
| | 2 | Acquisition |
| | 3 | Printer Busy |
| | 4 | Display Ready |
| | 5 | Parameter Access Control |
| | 6 | AC Line Monitor |
| | 7 | Stat Set Switch - Console |
| INP 3 | 0-7 | Printer-Clock Communication Port |
| INP 6 | 0 | IR Self Test |
| | 1 | MAG Self Test |
| | 2 | Implant Preference |
| | 3 | Preference |
| | 4 | Beeper |
| | 5 | Not Used |
| | 6 | Not Used |
| | 7 | Printer Self Test |
| INP 7 | 0-7 | Display Switch Decoder Row, Col |
| Q | | Programming Pulses |
| OUT 2 | 0 | IR Mux |
| | 1 | MAG Mux |
| | 2 | Drive Enable |
| | 3 | Telemetry Enable 1 |
| | 4 | Telemetry Enable 2 |
| | 5 | Acquisition Latch |
| | 6 | Clear Display |
| | 7 | Stat Set Backlight |
| OUT 3 | 0-7 | Printer |
| OUT 4 | 0 | Head Power |
| | 1 | Beeper |
| | 2 | Battery Test and Timer Reset |
| OUT 5 | 0-7 | Display |

It should be noted that interrupts are not used for responding to the operator or the implant. Instead, inputs such as telemetry and parameter selection via the overlay switch matrix appear as external flags. For example, when any one of the switch positions 28 (FIG. 3) on the overlay matrix is pressed EF 1 is activated. On the other hand, while the stat set button on the programming head activates EF 2, the statset panel switch 32 on the console is decoded at bit 7 of input port 2. In either event, the status of the switch is tested by software. In the case of EF 1, the accessing and testing of the bit are carried out in a single instruction. Data bytes for the printer are provided through input port 3. I/O port 3 is not shown in FIG. 11 since the instruction INP 3 puts the data on a data bus common to both the interactive programmer microprocessor and the printer microprocessor for 150 (FIG. 8) forming part of the printer control system 48. In contrast input port 7 accesses a byte of data representing which of the 120 overlay switches is depressed. INP 7 accesses the 8 bit I/O port U415 of FIG. 11. The preset dip switches 86 of FIG. 11 are accessed at I/O port 6. The data byte corresponds to eight separate switches two of which are not used at present. Three of the switches are used to by-pass or disable certain portions of the self test routine. These switches would be present to by-pass the particular feature that the user either did not have in his programmer or did not wish to use. Another switch disables the audible tone generator and two other dip switches correspond to the type of implant which the user intends to program. If the cardiac preference is chosen, it does not disable the programmer from programming neural implants but it does display initial screen messages relating to selection of the type of implant.

Programming is accomplished by modulating the Q output of the microprocessor on the microboard 116. Bits 0 and 1 of I/O port 2 steer the output to IR or MAG pulses, while bit 0 of utility port 4 accessed by device U414 connects power to the lead.

Figure 12A:
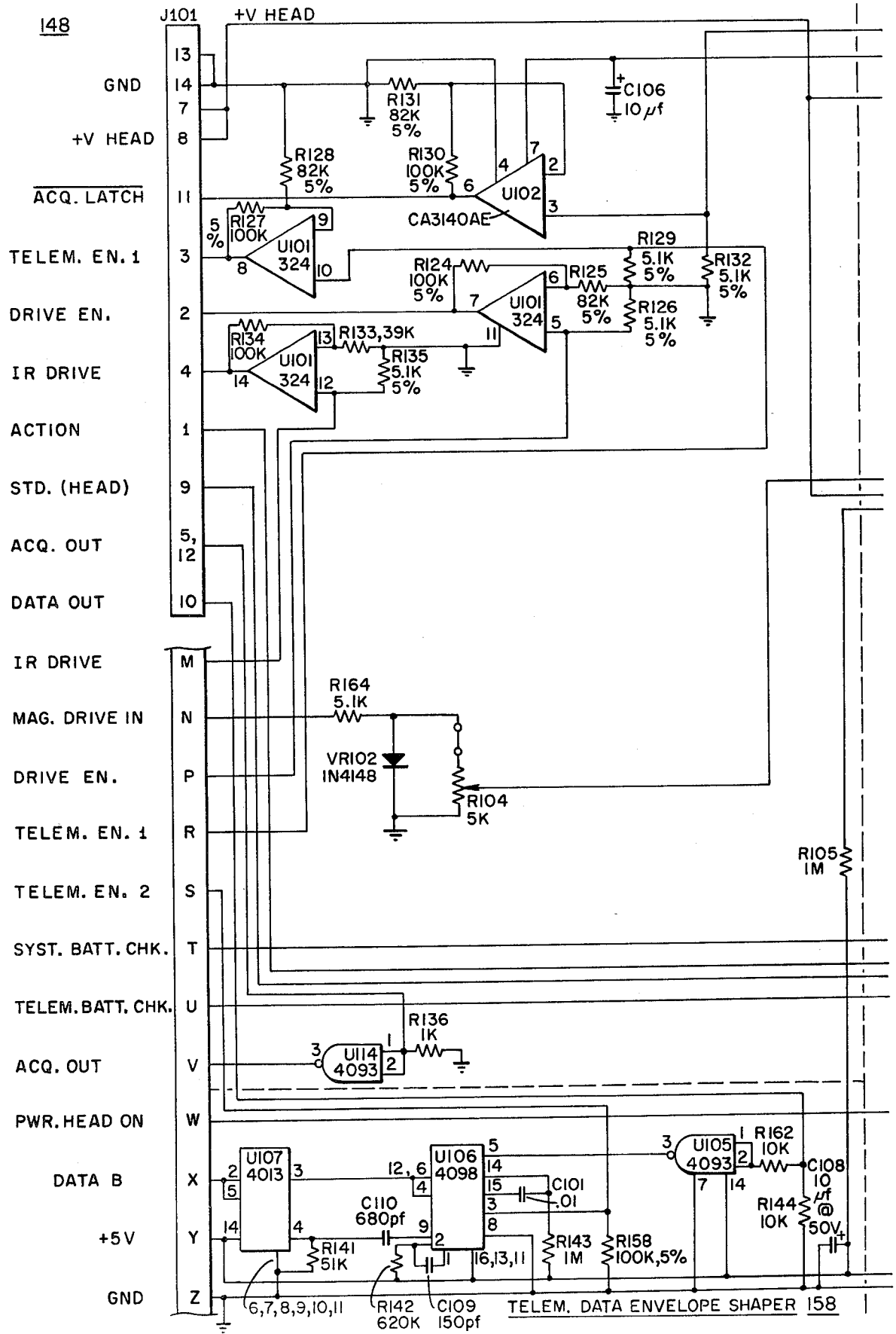
FIG. 12 is a block diagram of the analog I/O board of FIG. 8.
Figure 12B:
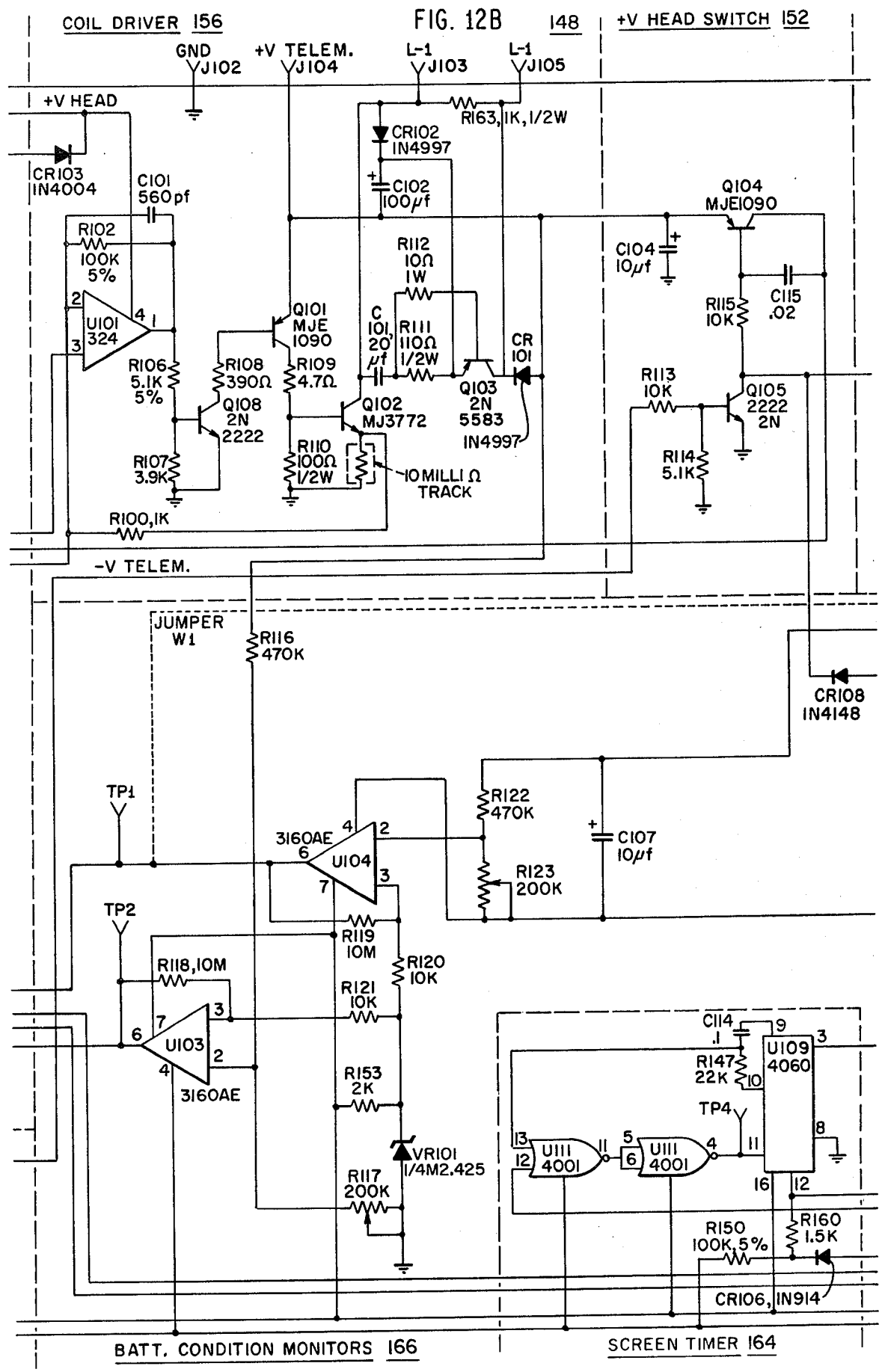
Figure 12C:
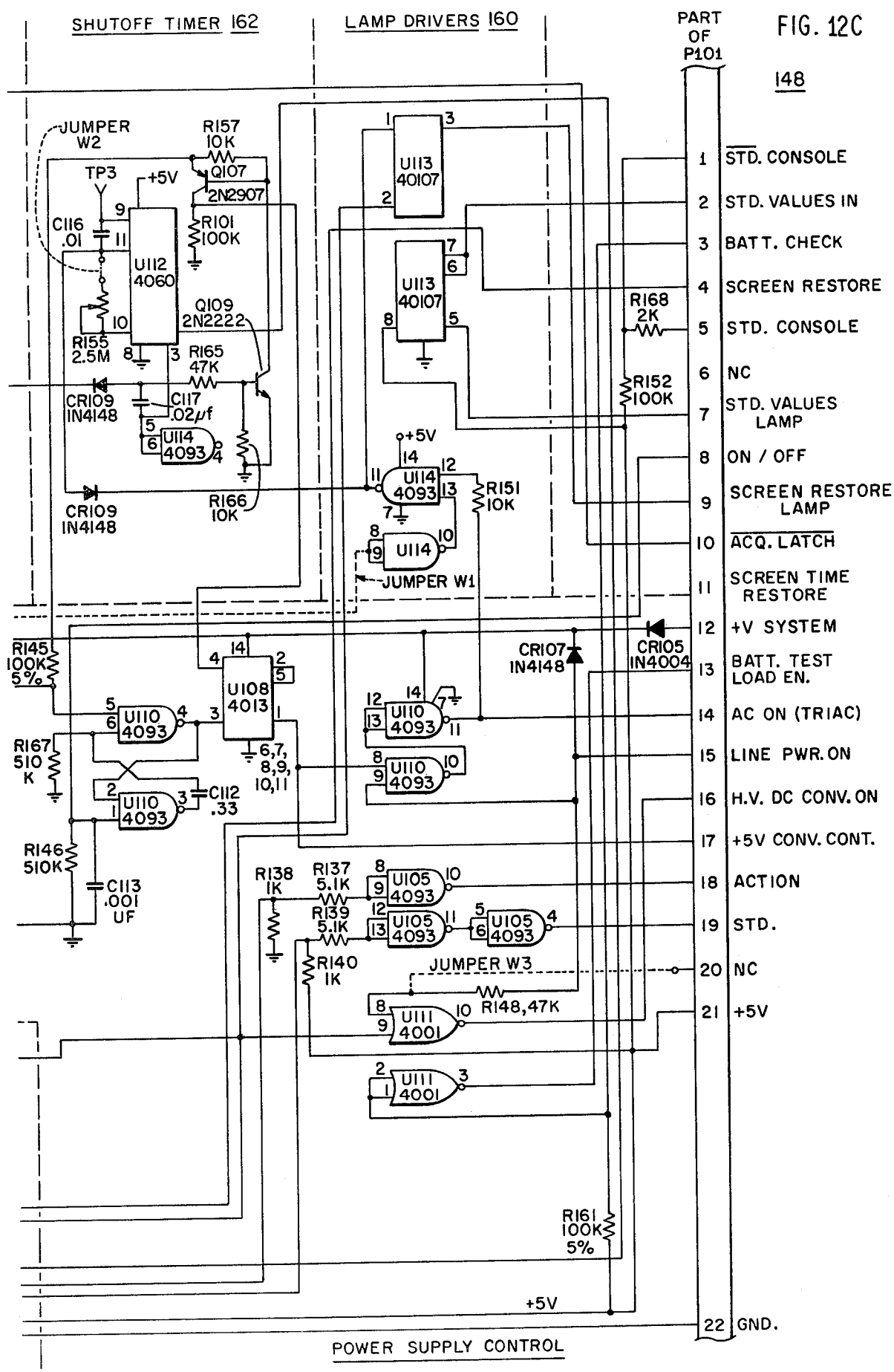
Figure 13A:
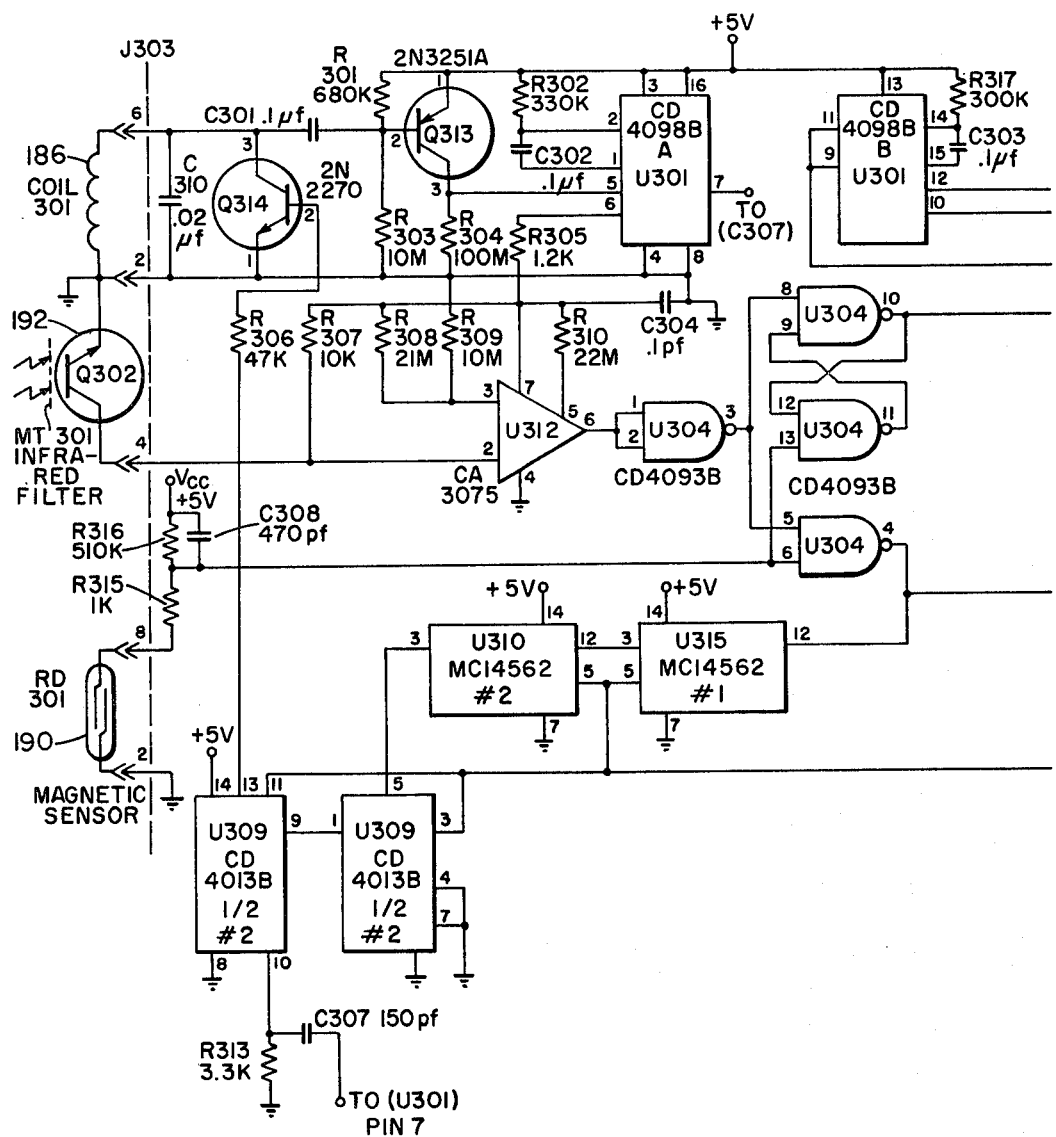
FIG. 13 is a block diagram of the self test circuit completing the digital I/O board of FIG. 8.
Figure 13B:
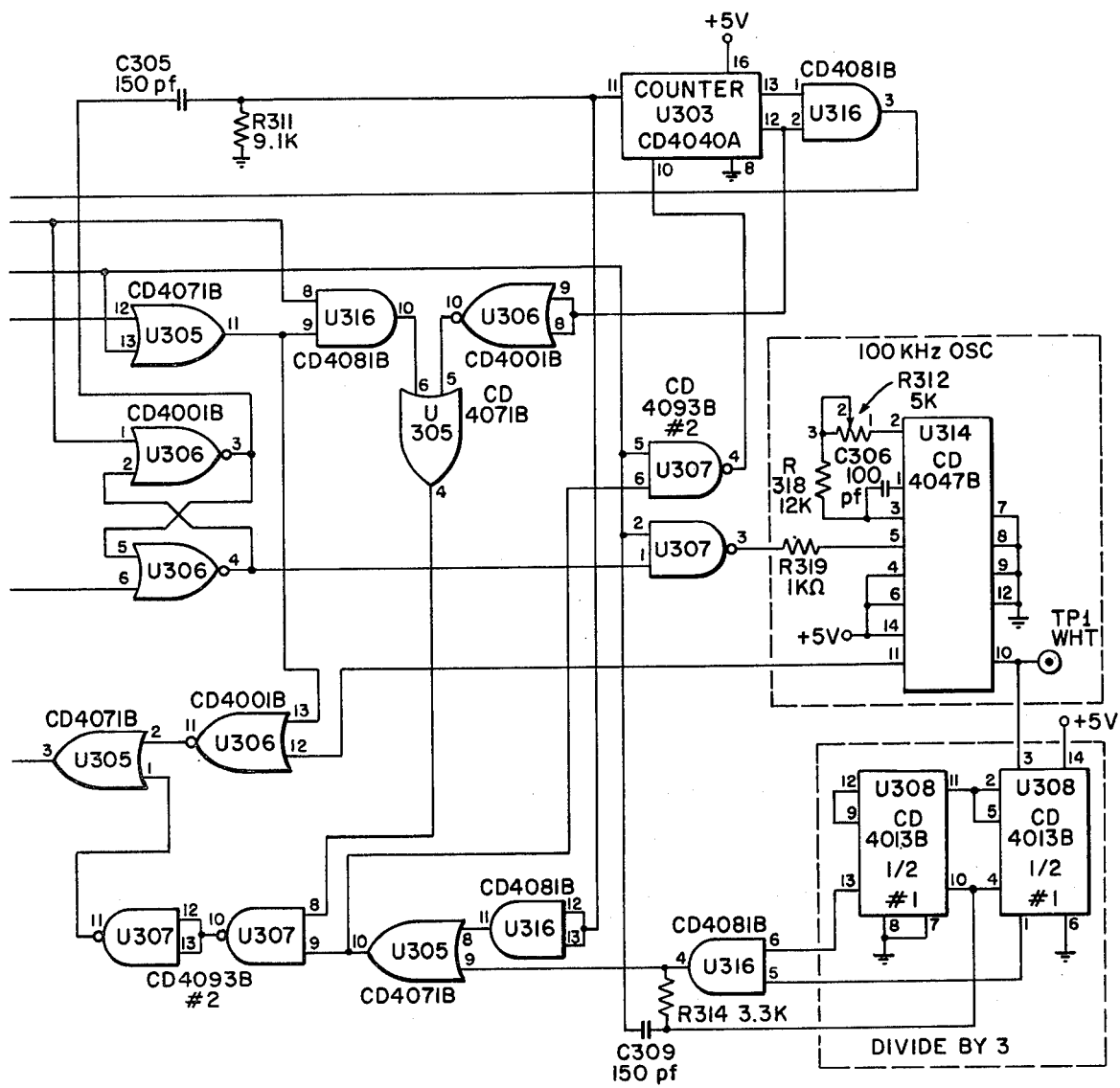

Throughout the block diagrams in FIGS. 11, 12 and 13 for the digital and analog I/O boards and self-test circuit, device designations for digital components, gates, flipflops, registers, etc. identify standard RCA CMOS digital integrated circuits. In the analog circuitry of FIG. 12, operational amplifiers U101U104 refer to standard linear integrated circuits available from Motorola or RCA for example.

Figure 8A:
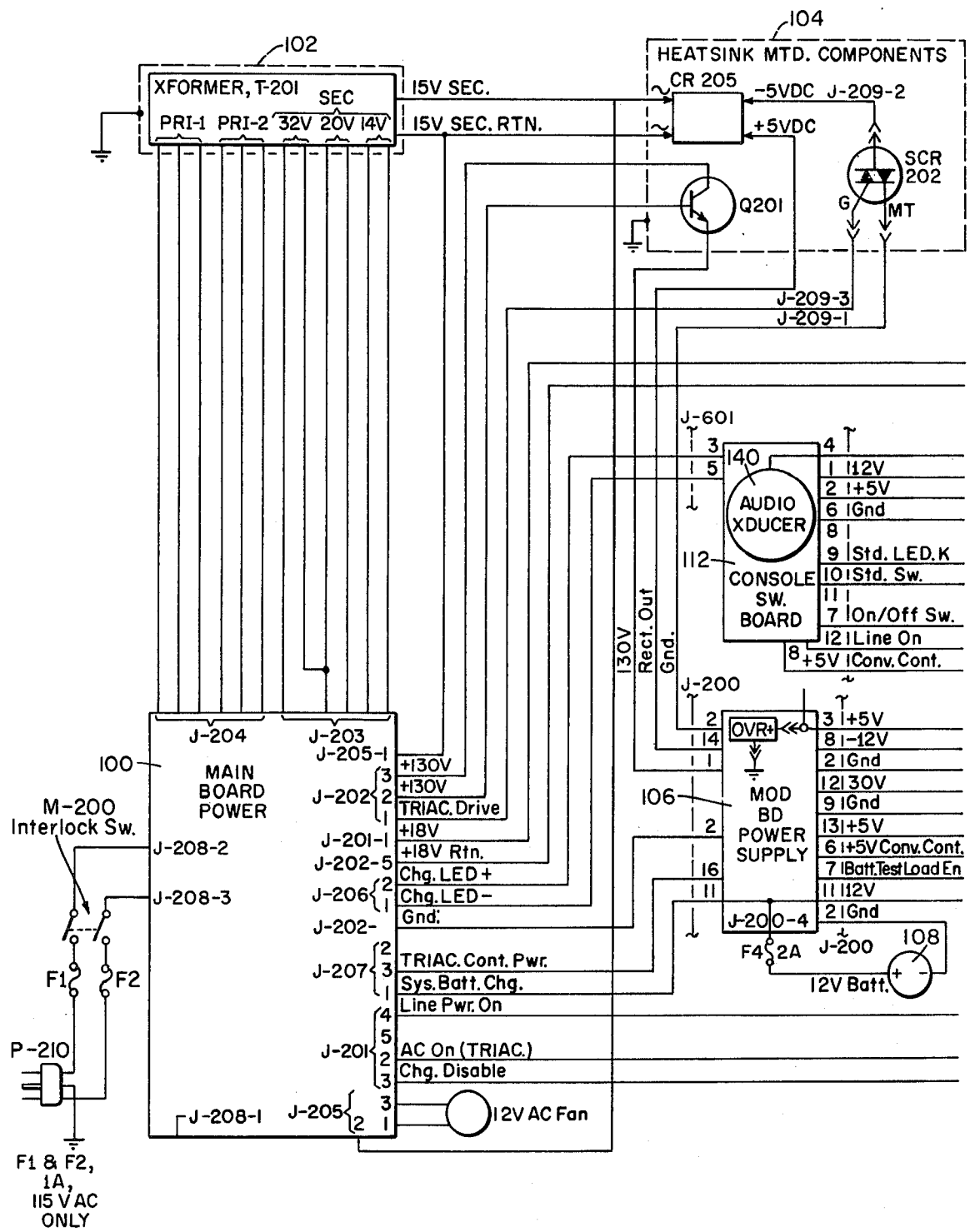
FIG. 8 is a wiring diagram for the electronics of the interactive programmer of FIG. 1.
Figure 8B:
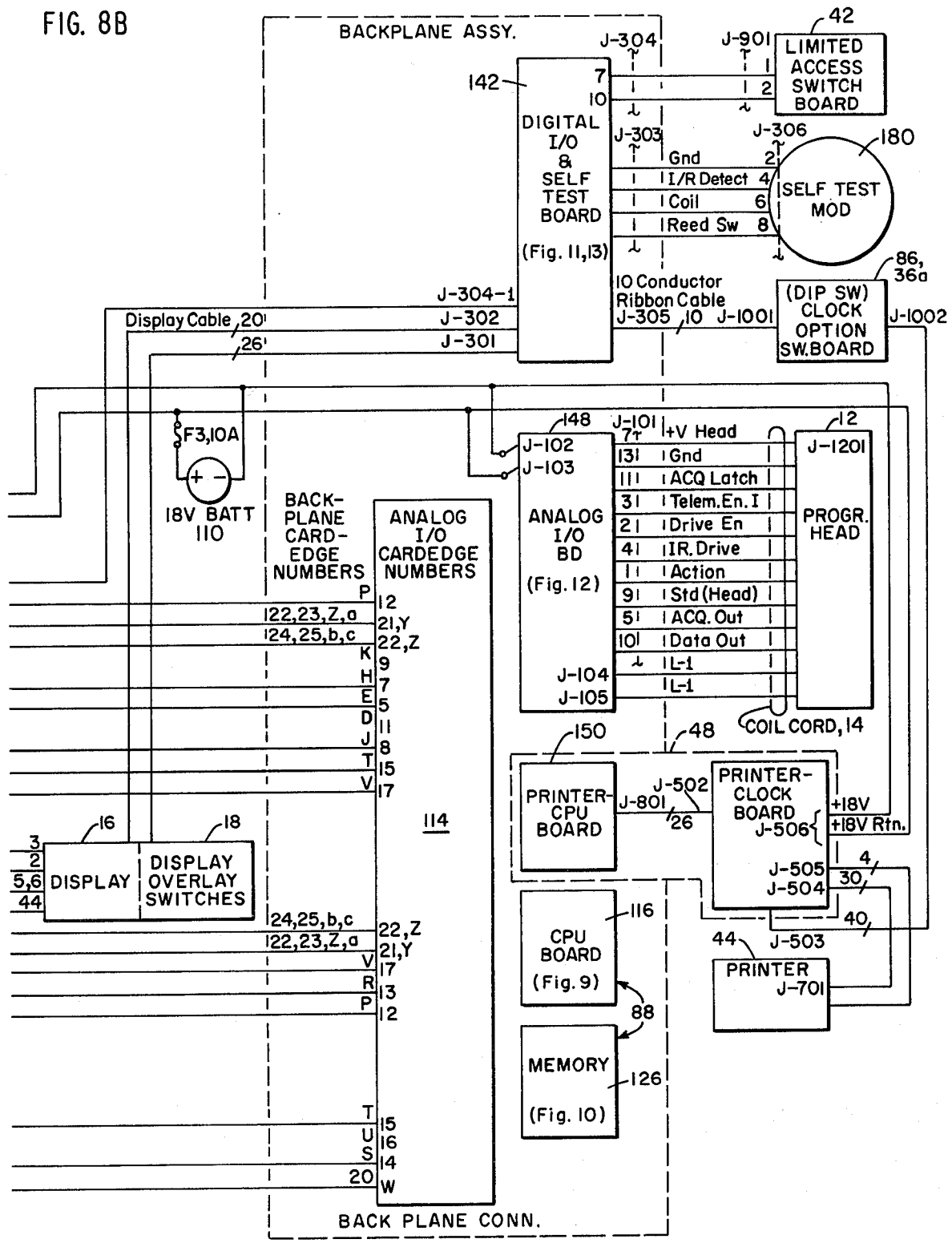
Figure 9:
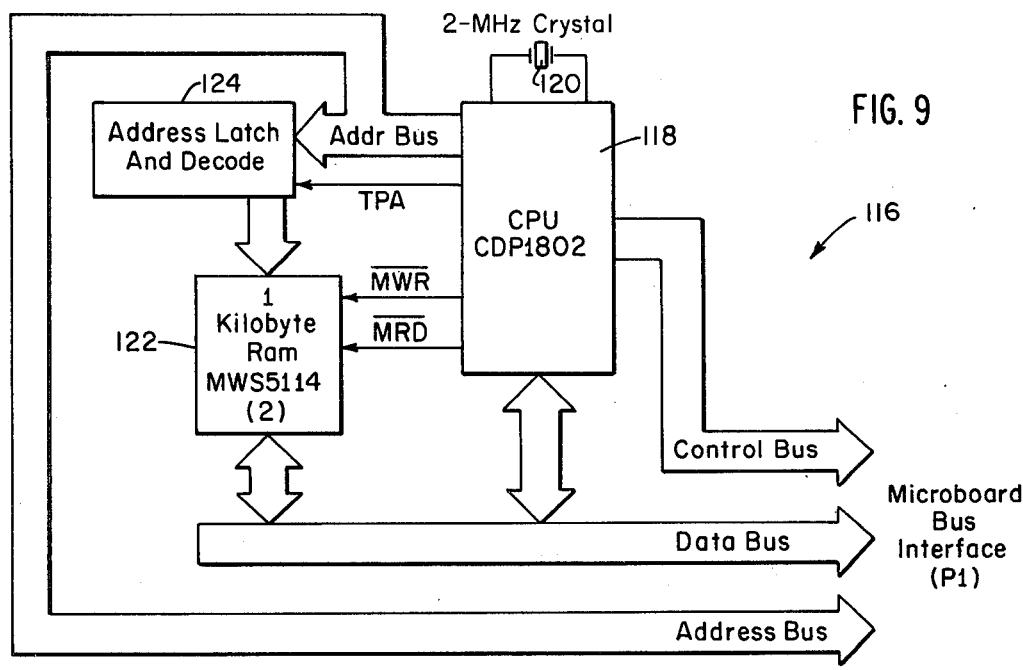
FIG. 9 is a block diagram of the CPU microboard of FIG. 8.
Figure 10:
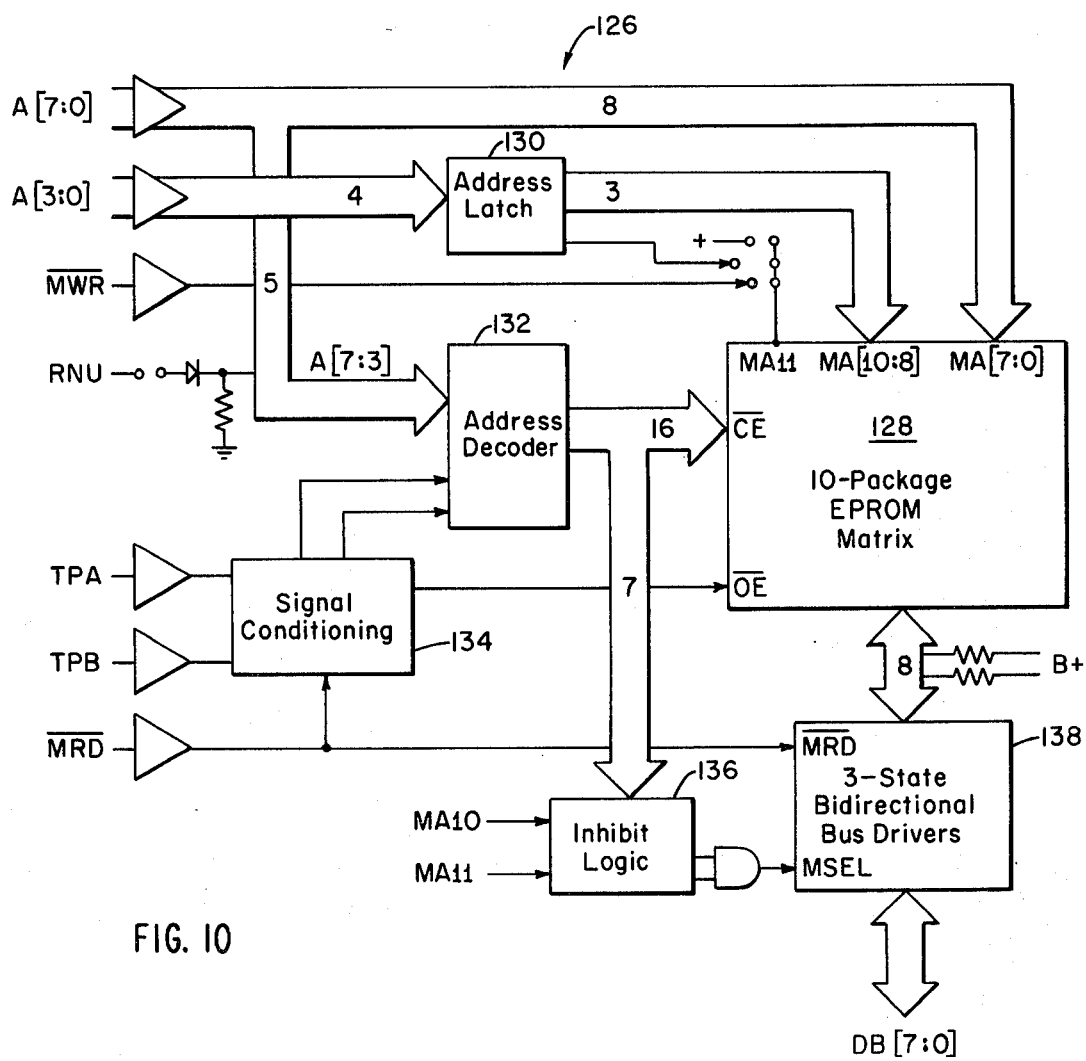
FIG. 10 is a block diagram of the memory microboard of FIG. 8.
Figure 11A:
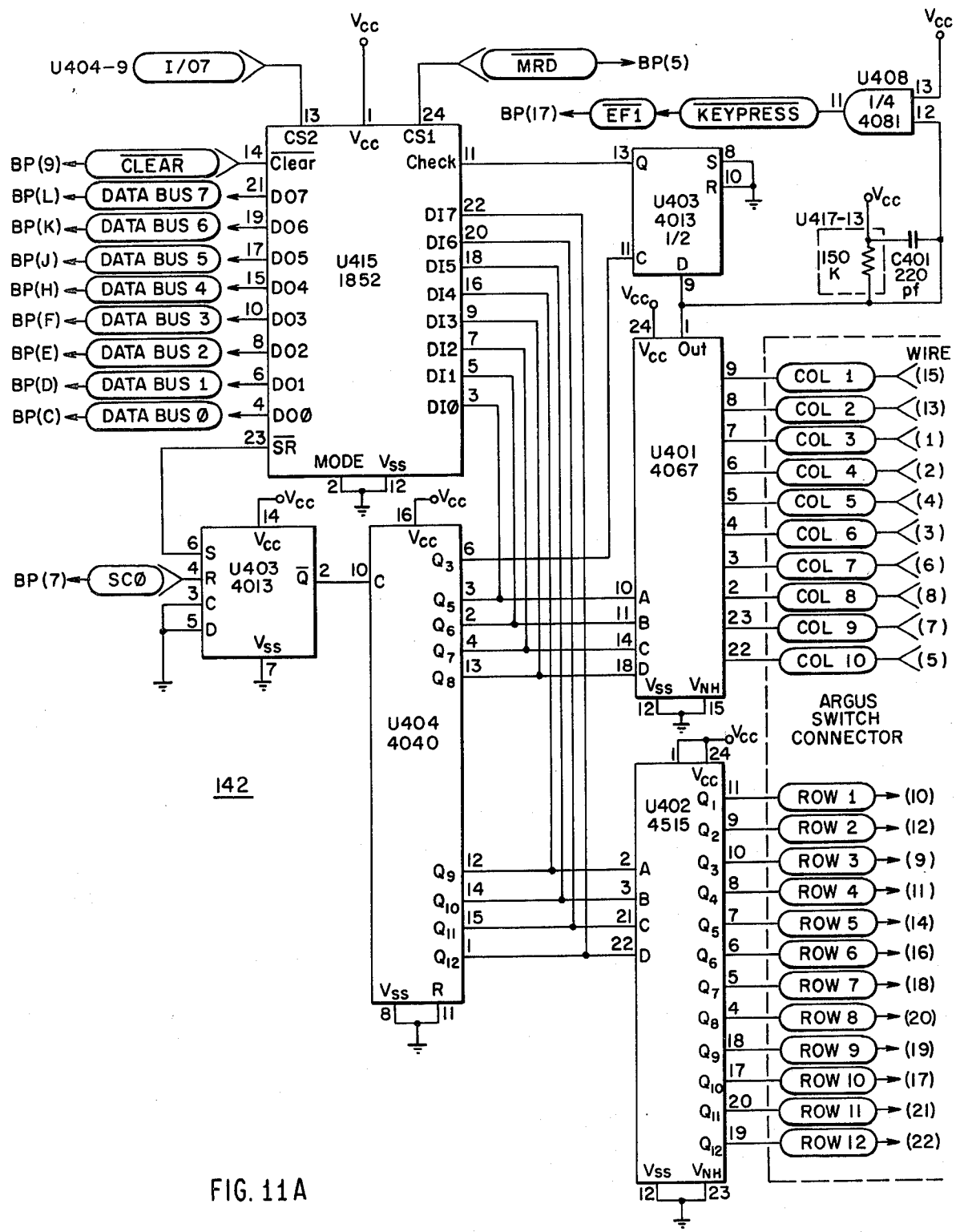
FIG. 11 is a block diagram of the digital I/O board of FIG. 8 except for the communications self test system.
Figures 11B, 11C:
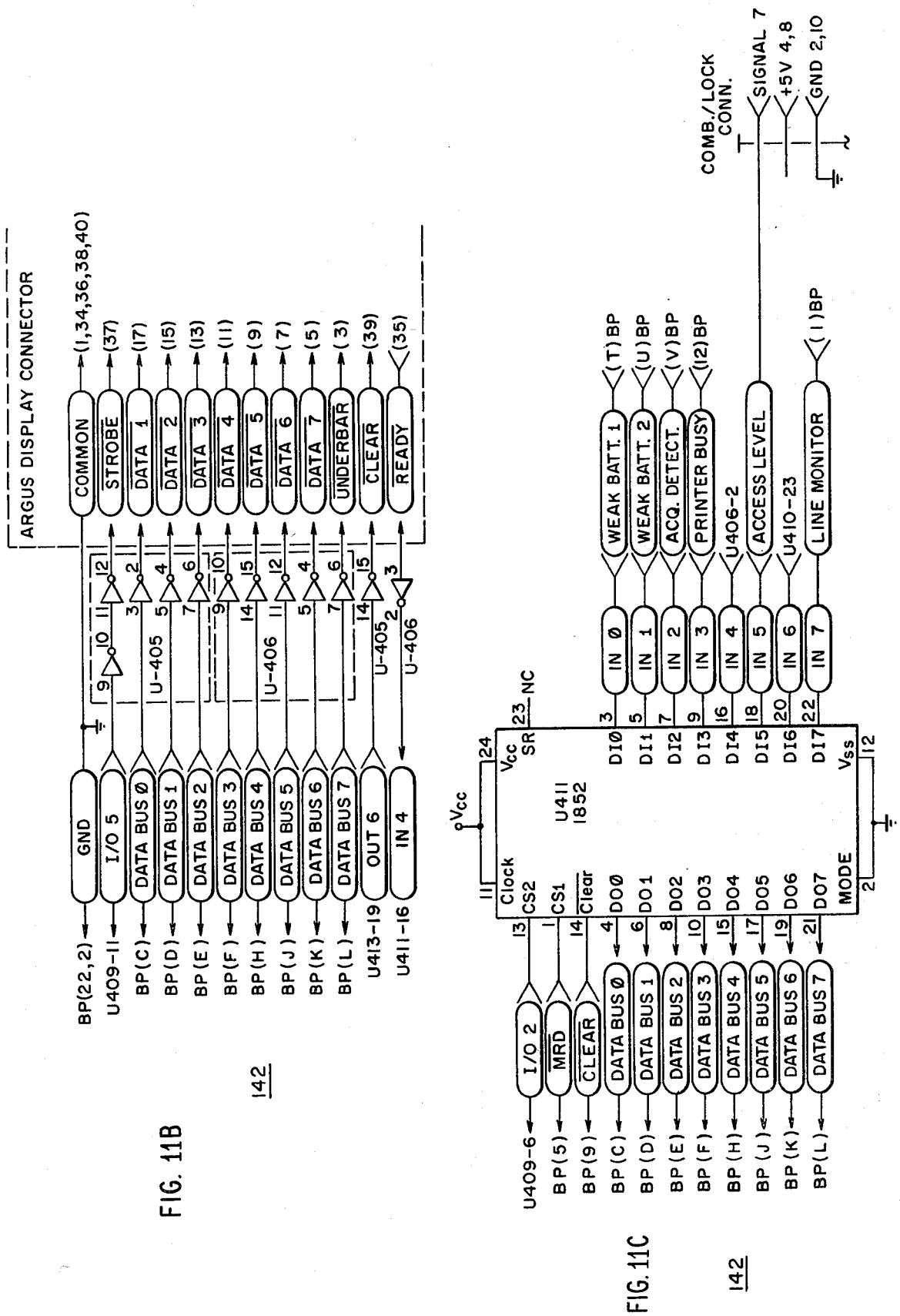
Figure 11D:
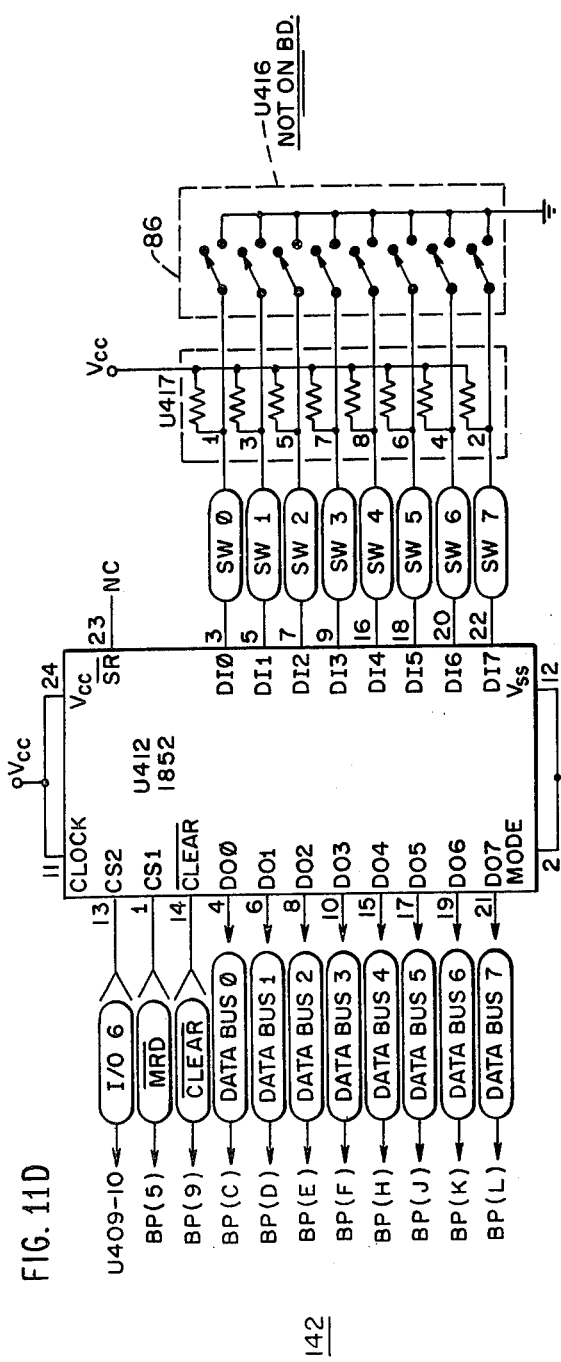
Figure 11E:
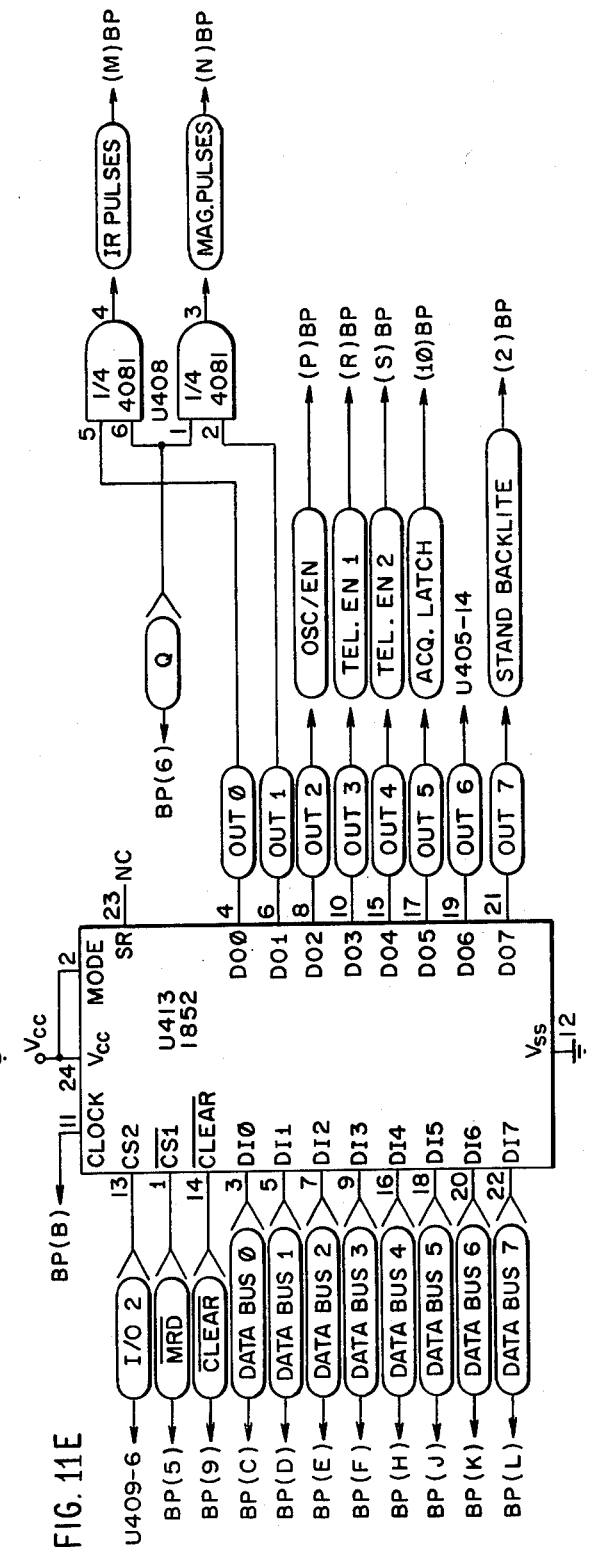
Figure 11F:
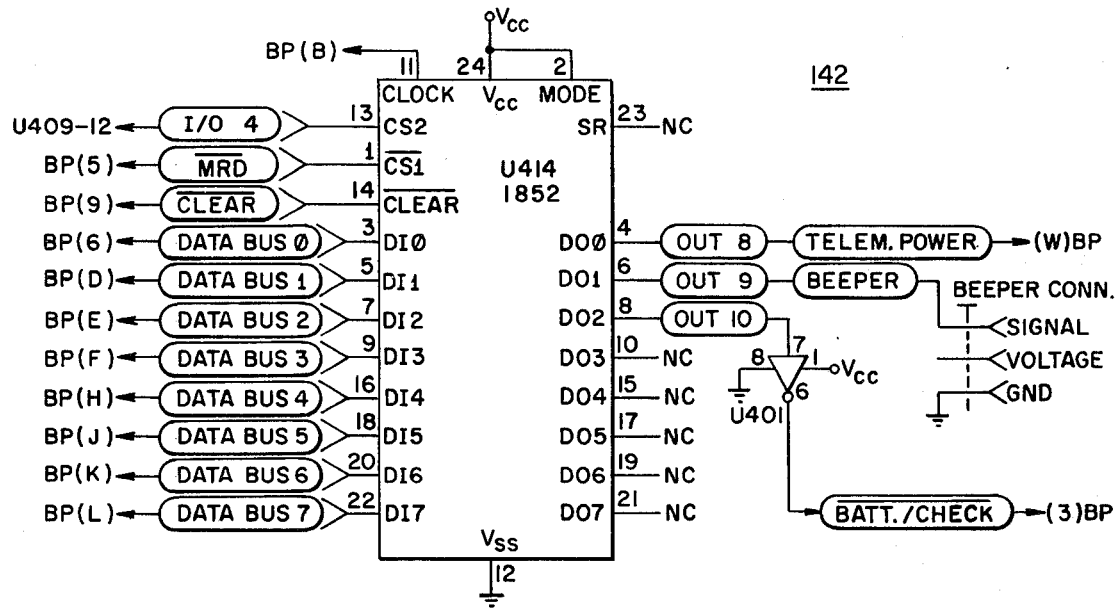
Figure 11G:
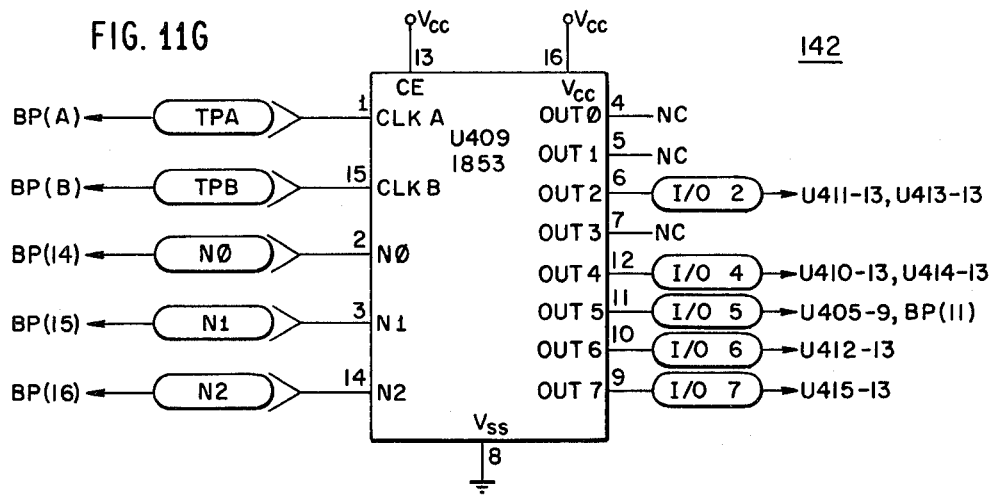

The purpose of the analog I/O board FIG. 12 is to interface the microcomputer comprising the CPU, memory and digital I/O boards shown in FIGS. 9, 10 and 11 with the programming head. The analog circuitry of FIG. 2 is mounted on the same kind of printed circuit card as the "microboards". The card has a card edge connector designated P101 to differentiate it from the backplane connector P1 common to the CPU, memory and digital I/O boards 116, 126 and 142. The card edge connector P101 has a number of connections in common with the backplane connector as shown in FIG. 8. All the designations for the card edge connector P101 are shown, however, in FIG. 12 in detail. A second connector on the analog card J101 provides ten output lines which extend to the programming head 12 via cable 14 as shown in FIG. 8. Head power is provided over the cable connector 8 in response to the power head ON signal at card edge pin W which operates the head switch circuit 152 of FIG. 12. A buffer circuit 154 has a plurality of isolation amplifiers interfacing head control signals from the microcomputer with the programming head. The acquisition latch signal on card edge pin 10 is produced by the fifth bit of the output byte transferred by the I/O port 2 (device U413, FIG. 11). From card edge pin 10, the acquisition latch signal is passed through a buffer amplifier U102 to pin 11 of the cable connector J101. Telemetry enable 1, drive enable and I/R drive are similarly buffered via amplifiers U101. The magnetic coil drive for the programming head is provided by coil driver circuit 156 on the analog board of FIG. 12. The signal to create a mag pulse is produced on digital I/O port FIG. 11 by I/O port 2 (device U413) in conjunction with the Q output of the microprocessor. The one bit of the output byte is ANDed with the Q signal to produce the mag drive IN signal to analog card edge pin N. This signal is coupled to a chain of amplifiers and signal conditioning circuitry shown in detail in the coil driver circuit 156 powered by the 18 volt supply via connector J103. The output of the coil driver circuit 156 is connected to cable connector J104 and J105 which interconnect the large programming coil in the head with the coil driver circuit 156.

The action and standard buttons on the head are connected via the cable connector pins 1 and 9 respectively to respective inverters U105 on the analog board and are presented on the card edge pins 18 and 19. Telemetry data in binary form from the programming head arrives over pin 10 of the cable connector J101 and is immediately passed through a telemetry data envelope shaper 158 whose output on card edge pin X duplicates the telemetry data input signal of the implant on line data B. Card edge pin X is connected directly to backplane pin X of the microcomputer system which is the EF4 input for data telemetry.

In addition to the head/console interface function, the analog board 148 has a number of other utility systems including lamp driver circuit 160, shut-off timer circuit 162, and screen timer circuit 164. The character strobe signal to the alpha numeric display is produced by I/O port 5, i.e., by software. The strobe signal is connected via a pair of inverters (U405) to pin 37 of the display connector and also to analog card edge pin 11. Although absent in the present embodiment shown in FIG. 12, the signal on card edge pin 11 can be used to continuously retrigger the screen timer 164. The strobe signal (screen time restore) is present only when a new display is created. Thus, if a new display has not been created for thirty seconds, for example, the screen is blanked if there has been no change. The strobe signal (screen time restore) resets the timer in effect each time a new display is presented. Although not present in this embodiment, the screen timer 164 also actuates one of the lamp drivers U113 to light a screen restore lamp via card edge pin 9.

Shut-off timer 162 is used for timing the battery self test function. A battery check input signal on card edge pin 3 is buffered to produce the battery test load and enable signal on card edge pin 13. At the same time the battery check signal causes a shut-off timer to disconnect the line current supply to the battery chargers while a dummy load is placed across the batteries. Battery condition monitors 166 continuously compare the system voltage and telemetry voltage to a reference voltage level. Differential amplifier U104 is connected via card edge pin 12 to system voltage and produces an output to card edge pin T for system battery checkpoint while differential amplifier U103 is connected to telemetry voltage via the J103 connector and produces a telemetry battery checkpoint at card edge pin U.

Figure 5:
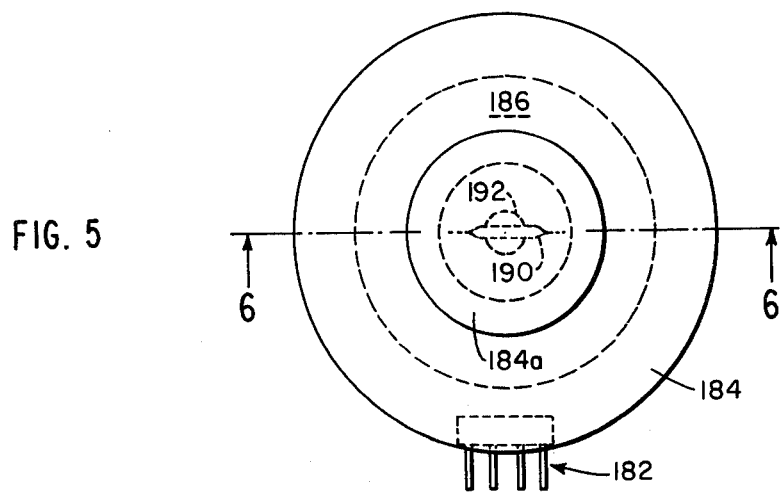
FIG. 5 is a plan view of the self test module.
Figure 6:
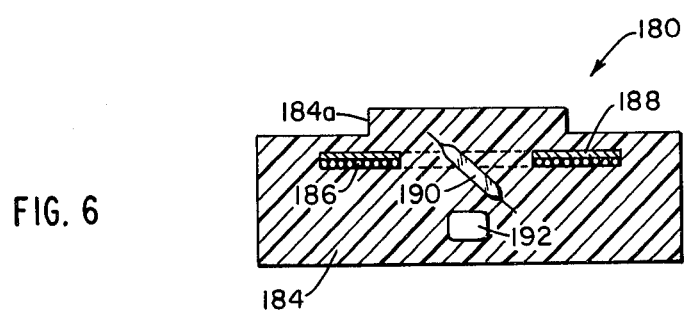
FIG. 6 is a sectional view taken along lines 6—6 of FIG. 5.

The digital I/O board 142 is shared with a communication self test system shown in FIG. 13. The interactive programmer is designed to work with implants which are programmed via reed switch closures or some other magnetic sensor in response to the magnetic coil in the head or by pulsed I/R. The programmer is also designed to receive data from an implant by means of the shunted tuned coil system described in U.S. Pat. No. 4,361,153. The communication transducers of the implant are duplicated in the programmer in self-test module 180 shown physically in FIGS. 2, 5 and 6 and electrically in FIGS. 8 and 13. The self-test module 180 includes cable connector pins 182 and a puck-shaped body 184 of suitable potting material having a coaxial boss 184a. The module 180 encompasses the electrical implant communications transducers. Flat coil 186 is coaxially mounted in the module 180 on a substrate 188. A reed switch 190, or equivalent magnetic sensor, is centrally located in the module 184 inclined at 45° to the axis. The I/R sensitive device is provided by a photodiode 192 located on the axis below the reed switch 190. The epoxy potting material preferred for the self-test module 190 is tinted with IR transparent red pigment. The electrical leads from the transducers 186, 190 and 192 are connected to the cable connector pins 182 with a common ground connection. The connector pins 182 are in turn connected by a cable to the self-test circuit on board 142 as shown in FIG. 13. As shown in FIG. 2, self-test module 180 is positioned in selftest module bracket 94 within the console 10 at the bottom of the cradle 10c for the programming head 12, boss 184a being received in a mating aperture in the floor of the cradle 10c such that the test module 180 is approximately coaxial with the cradled programming head 112.

The self-test of the communications links verifies the operation of three separate functional capabilities. The first is the ability of the programming head to detect the presence of the implant within programming range, the "acquisition" function. The second is the ability of the programming head to output sufficiently accurate magnetic programming pulses and to receive these back from the implant via the telemetry data transfer function. The last is the ability of the programming head to output sufficiently accurate infrared programming pulses and to receive these back via the telemetry data function. The communications self-test system 84 (FIG. 7) includes the interconnected self-test module 180 and the self-test circuit of FIG. 13. The self-test circuit of FIG. 13 incorporates sufficient circuitry to allow the system to receive magnetic or infrared programming inputs, sample them rapidly enough to retain their timing accuracy and return them to the programming head via the telemetry coil. The communications testing electronics need not be connected to the interactive programmer electronics; rather it is sufficient for information to be relayed to the test circuitry by the programming head 12, stored in the test circuitry of FIG. 13 and then relayed back to the interactive programmer console 10 via the programming head 12. However, it is desirable for this test circuitry to be physically attached to the interactive programmer console so that it is continuously available. For this reason, it was decided to install the necessary input/output transducers (read switch 190, infrared sensor 192 and telemetry coil 186) inside the interactive console 10, immediately below the programming head cradle. Thus, when the programming head 12 is in its cradle, it is correctly oriented to communicate with the sensors located inside the programming console. The additional circuitry necessary to receive, store and retransmit the communications test signals is located on card 142 along with digital I/O circuits in the main electronics card cage. However, its only connection to the rest of the programmer electronics is that it uses the same power supply.

The actual communications link self test procedure begins by turning on the telemetry transmitter (DRIVE ENABLE) in the programming head 12 and looking for acquisition of the programming console's implanted coil. If acquisition is not detected, the user is asked via the display screen whether the programming head is in the cradle. If it is, then the acquisition function is assumed to be non-functional. If it is not, he is asked to place it in the cradle and indicate on the display screen when he has done so. The system will then test again for acquisition.

Once acquisition has been detected, the testing of the magnetic programming link is begun. The microprocessor 88 (FIG. 7) outputs via the magnetic programming coil in the head 12 a 6 msec pulse train, including pulses of 0.75, 1.0 and 2.0 msec duration. These pulses are detected by the magnetic reed switch and stored in the shift registers of the self test electronics circuitry. The self test circuitry of FIG. 13 then feeds these signals out at a 1 kilobaud equivalent rate via the telemetry output function. The telemetry data signal is detected in the programming head 12, decoded and fed back to the microprocessor 88. The microprocessor then compares the transmitted and received signals to determine whether or not the system is functioning properly.

Regardless of the results of the magnetic programming test, the system repeats a similar test for the infrared programming link. The primary difference between the infrared and magnetic test is that the infrared pulse train does not include the 0.75 msec programming pulse and that the telemetry data is transmitted back at 333 baud, rather than 1 kilobaud.

These two tests allow the programmer to determine the independent functional capabilities of three communications links. If the magnetic test fails and the infrared test is passed successfully, the magnetic programming output is faulty, while the telemetry and infrared functions are working properly. Similarly, failure of the infrared test with successful completion of the magnetic test would identify the failure as being in the infrared programming outputs. Failure of both tests would indicate the probable failure is in the telemetry data link.

The circuit of FIG. 13 can be divided into two general modes of operation. The first mode being the reception of infrared pulse width data from the programming head 12, the storing of this data in serial registers, and the transmission of this data using the passive magnetic telemetry channel. The second test mode is reception of magnetic programming pulses, the storing of this data, and the transmission of this data using the passive magnetic telemetry channel. Both of these modes require that acquisition has occurred.

Mode 1: With the programming head 12 placed over the self test module 180 (FIG. 2), 16 kHz electromagnetic energy is applied to the telemetry coil, which is amplified by Q313 and turn on IR enable one-shot U301A in FIG. 13. When this happens, the infrared circuits are powered up, and any infrared pulses present will be amplified by Q302 and U312. The amplified pulses are routed to gate Q304 (pins 1 & 2) which inverts the data signal and toggles a flipflop composed of two AND gates U304 (pins 10 and 11) and sets the return data clock rate so that the infrared data is transmitted back at the same rate as it is received. When U304 (pins 10 and 11) is set in the other state (reed switch programming) the data is transmitted back at a rate three times as fast as it is received. The output of U304 (pin 4) is connected to the inputs of the 128 bit static shift register, U315, and U306 (pin 6). When data appears on U306 (pin 6), pin 3 (U306) will latch high and reset U303 (program counter).

The pulse used to reset U303 is also used to trigger U316 (pulse stretcher) which introduces enough delay so that when this output appears at U307 (pin 10) it serves as the first clock pulse. Without this circuit the first clock pulse would be missing. With one input to U307 (pins 1 and 2) low and the other input high, pin 5 of Q311 is held high and the clock oscillator will run. With pin 8 (U307) held high by the program counter, clock pulses can now pass through U307 and U305 and will cause the shift register to shift one bit for each pulse it receives. As this is happening, the program counter counts each pulse and will turn off the clock pulse U310 and U315 when its count reaches 256 (2). The clock pulses are obtained from a true-gated astable circuit U311, which is running at 100 kHz. This frequency is divided by three by flipflops U308. The 128 bit shift registers U310 and U315 and the program counter U303 are stepped at 100 kHz or 33 kHz. This stepping rate is used for both the incoming infrared signal and the outgoing telemetry signal.

When the program counter U303 reaches a count of 256, U306 (pins 8 and 9) is triggered, which stops the flow of clock pulses to the shift registers. This action is the result of flow of commands through U306 (pin 10), U305 (pin 4), and U307 (pin 8). It should be noted that neither the clock nor the program counter has been stopped by this action. The program counter counts another 128 counts and then triggers one-shot U301 (B). When this occurs, clock pulses to U303 are stopped. U301 (pin 10) now restores the clock pulses to the shift registers through U316, U305, and U307. U309 provides two additional storage registers. As the data is transferred out of the storage register, transistor Q314 is turned on and off, which shorts out coil 186 (L301) for telemetry. When the data is being shifted out of the shift registers, their input is held low and this clears all stored data from them. One-shot U301 (B) allows enough time for the stored data to be removed and then rests all circuits to a receive mode.

Mode 2: With the programming head placed over the self test module, 16 kHz electromagnetic energy is applied to the telemetry coil which reflects a signal to the programming head indicating acquisition. When the reed switch 190 (RD301) is operated by magnetic programming pulses from the head 12, electrical pulses are generated, which toggle flipflop U304 (pins 10 and 11 so that the data dump rate is three times the rate as data storage rate. The output of U304 (pin 4) is connected to the input of the shift registers U315 and flipflop U306 (pin 6). When data appear at U306 (pin 6), pin 3 (U306) will latch high and reset U303 (program counter).

The pulse used to reset U303 is also used to trigger U316 which introduces enough delay so that when this output appears at U307 (pin 10), it serves as the first clock pulse. With one input to U307 (pin 1 and 2) low and the other input high, pin 5 of U311 is held high and the clock oscillator will run. With pin 8 (U307) held high by the program counter, clock pulses can now pass through U307 and U305 and will cause the shift register (U310, 315) to shift one bit for each clock pulse it receives. As this is happening, the program counter counts each pulse and will turn off the clock pulses to U310 and U315 when the count reaches 256, which is the combined storage of U310 and U315. The clock pulses are obtained from a monostable oscillator U311, which is running at 100 kHz. This frequency is divided by three by U308 and U306. The shift registers U310 and U315 and the program counter U303 are stepped at 100 kHz or 33 kHz. This rate is only used in the loading mode. A 100 kHz clock rate is used in the dump mode'.

When the program counter reaches a count of 256, U306 is triggered, and the flow of clock pulses to the shift register is terminated. The routing for this command flows through U306 (pin 10), U305 (pin 4), and U307 (pin 10). The program counter and the clock are still running and the program counter will count another 128 counts and then trigger U301 (B). When this occurs, clock pulses to U303 stop.

Earlier in this mode, U304 was set to allow the clock rate to be full rate during the dump cycle. With U304 (pin 10) low clock pulses are allowed to flow from U311 (pin 11) through U306 (pin 11), U305 (pin 3) to the shift registers (U310 and U315). The stored data is now moved out of the shift registers to operate transistor U314. When a high level is shifted to U314, it turns on and shorts the telemetry coil. As the data is shifted out of the shift registers, no new data is entered so that after all the data is shifted out, the registers are clear of stored data.

U301 (B) now times out and will reset the latches and the clock routing and turns off the oscillator. The circuit is then ready to receive in either mode of operation.

The microprocessor system 88 comprises CPU board 116, EPROM board 126 and the digital I/O porton in FIG. 11 of board 142. The outputs of this microprocessor system control directly most of the functions of the programmer including the display, illumination or activation of buttons and lights on the console and programming head, the programming transmissions and audio tone. All of these operations are controlled by a set of instructions stored in the microprocessor EPROM board 126. The sequence of instructions or software directs the sequence and timing of all microprocessor controlled operations. The software not only controls the sequence of operations but actually carries out the formation of the programming pulses to the implant. For example, magnetic or IR pulses are created directly by software control of the Q port of the microprocessor chip.

The software instructions residing in the memory are in the form of binary ones and zero's. The machine code instructions are typically designated in hexidecimal digit form, one byte of eight bits requiring two hex digits. Similarly, the address of any given byte memory is provided by four hex digits.

The software associated with the microprocessor system for the interactive programmer is organized into a plurality of modules referred to as Subparts A through N. Subpart A is an equate table module which, beginning at page 2 designates shorthand lables for fixed numbers at identified memory locations. Subpart B defines the macro instructions which are labels that the assembler recognizes as shorthand for a short series of instructions which are specified in assembly language. These labels are used by the programmer in composing the program. The software actually begins in Subpart C with the self test module. The self test module is divided into consecutive sections for the various tests. The main program module is contained in Subpart D module. Subpart E contains the Omnicor and neural 900 series main program for the interactive programmer. This routine programs the operations illustrated in FIG. 16A-16D and FIG. 17 for the Omnicor series of cardiac pacers and the Cordis 900 series of neural stimulators. All these implants have no telemetry and are programmed by magnetic impulses in a similar manner. Subpart F is the main software module for Multicortype pacers. The operation is illustrated in FIGS. 18A-18H and FIG. 19. Subpart G contains the software main module for Gemini-type pacers which are programmed with binary pulse width modulated magnetic impulses and do have telemetry. Subpart H is the main program module for programming Sequicor-type pacers of the type described in copending application Ser. No. 207,003. Subparts I, J, K and L contain programming sub-routines. Subpart M is the I/O sub-routine module. Subpart N contains the printer module. Subpart O contains the message module containing all of the overlay messages for the display and finally Subpart P is the tables module containing lists of the memory addresses and values of the programmable parameters.

Figure 14:
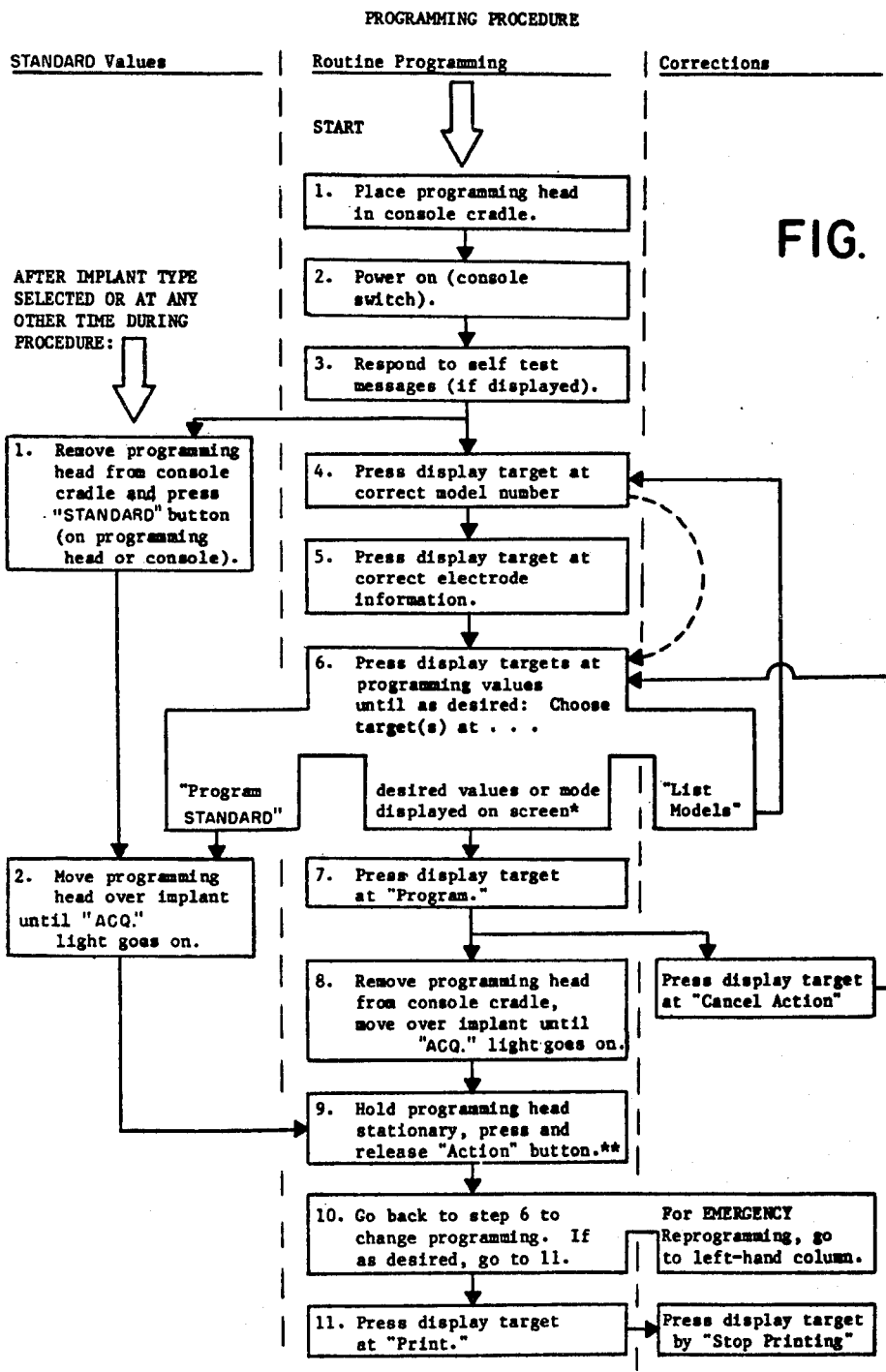
FIG. 14 is a flow chart of the programming sequence.
Figure 15B:
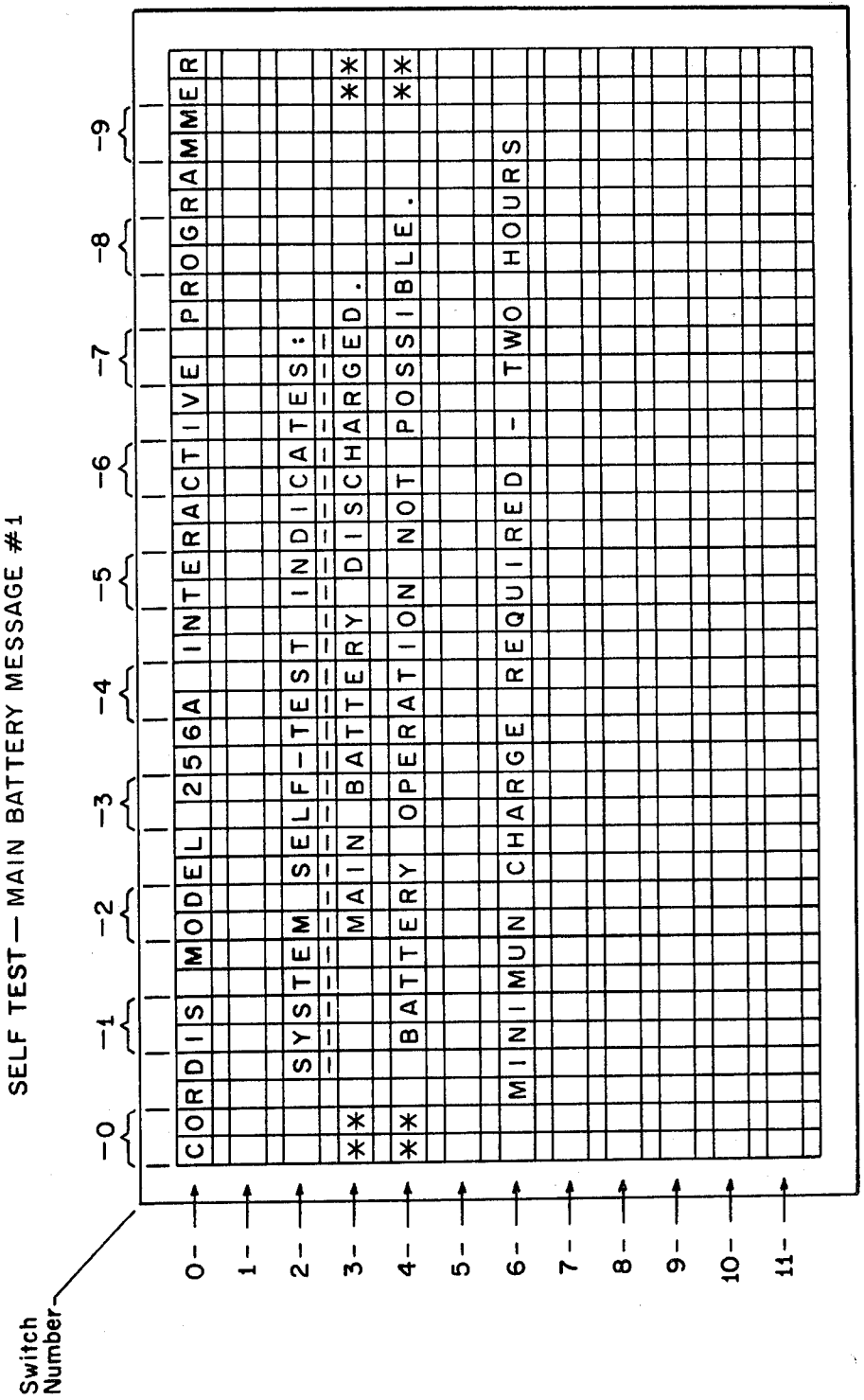

FIG. 14 illustrates a typical programming procedure for a non-telemetry implant. The programming routine is started with the programming head 12 in the console cradle 10c. On turning on the power with the ON/OFF switch 32, the interactive programmer automatically goes through a self test procedure. The programmer automatically displays the format of FIG. 15A to tell the user that the self test routine is in progress. The software automatically tests the main battery voltage, the random access memory, the EPROM containing all of the software instructions, the programming battery, the programming communications systems and the printer. The name of each test comes up on the screen as in FIG. 15A. When each test starts, the name of the test dashes, and OK appears when the test is satisfactorily completed. The message of FIG. 15B appears when the system is operating on line voltage rather than the main battery. The message of FIG. 15B is displayed for three seconds and then the self test sequence is resumed.

Figure 15D:
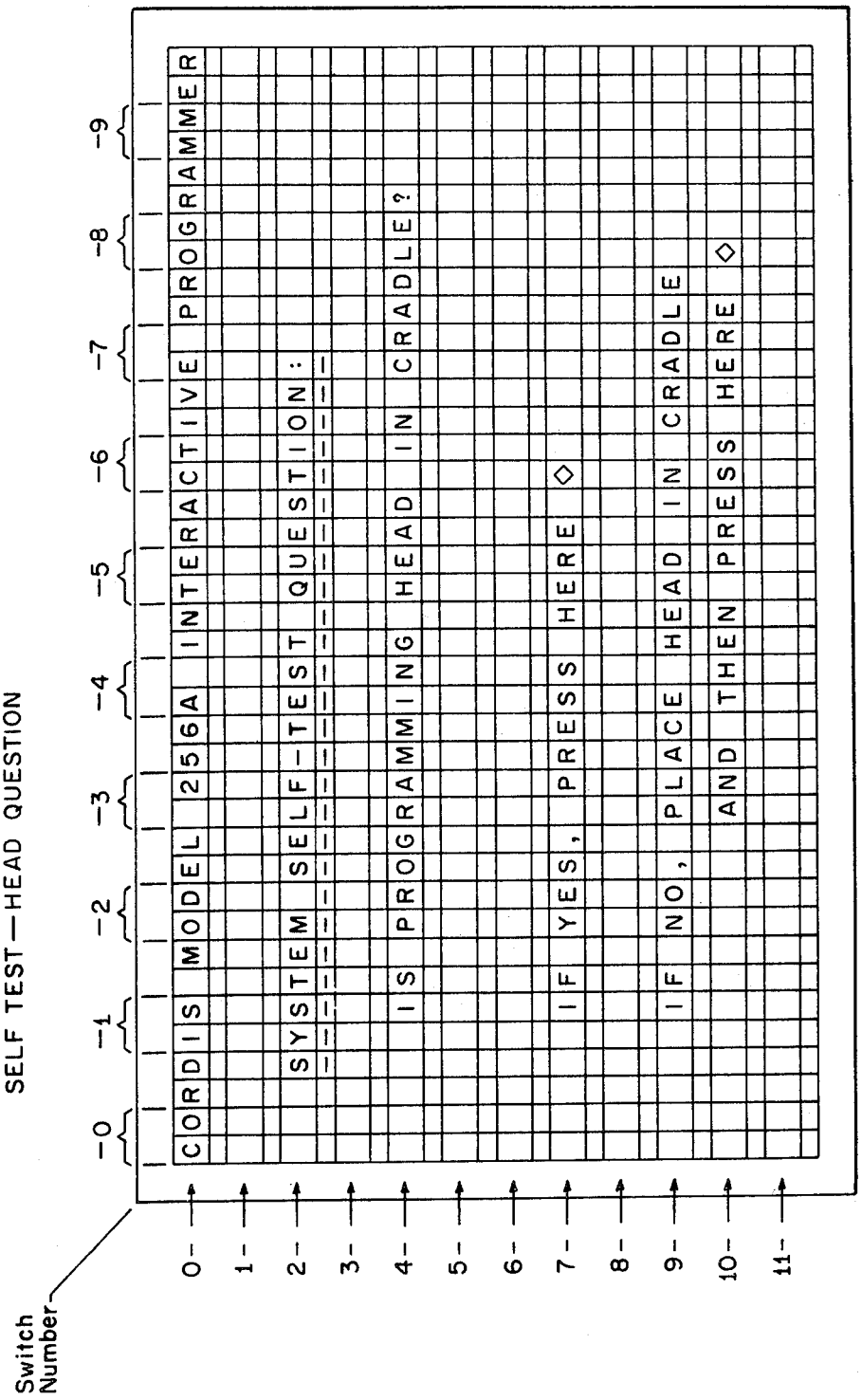
Figure 15H:
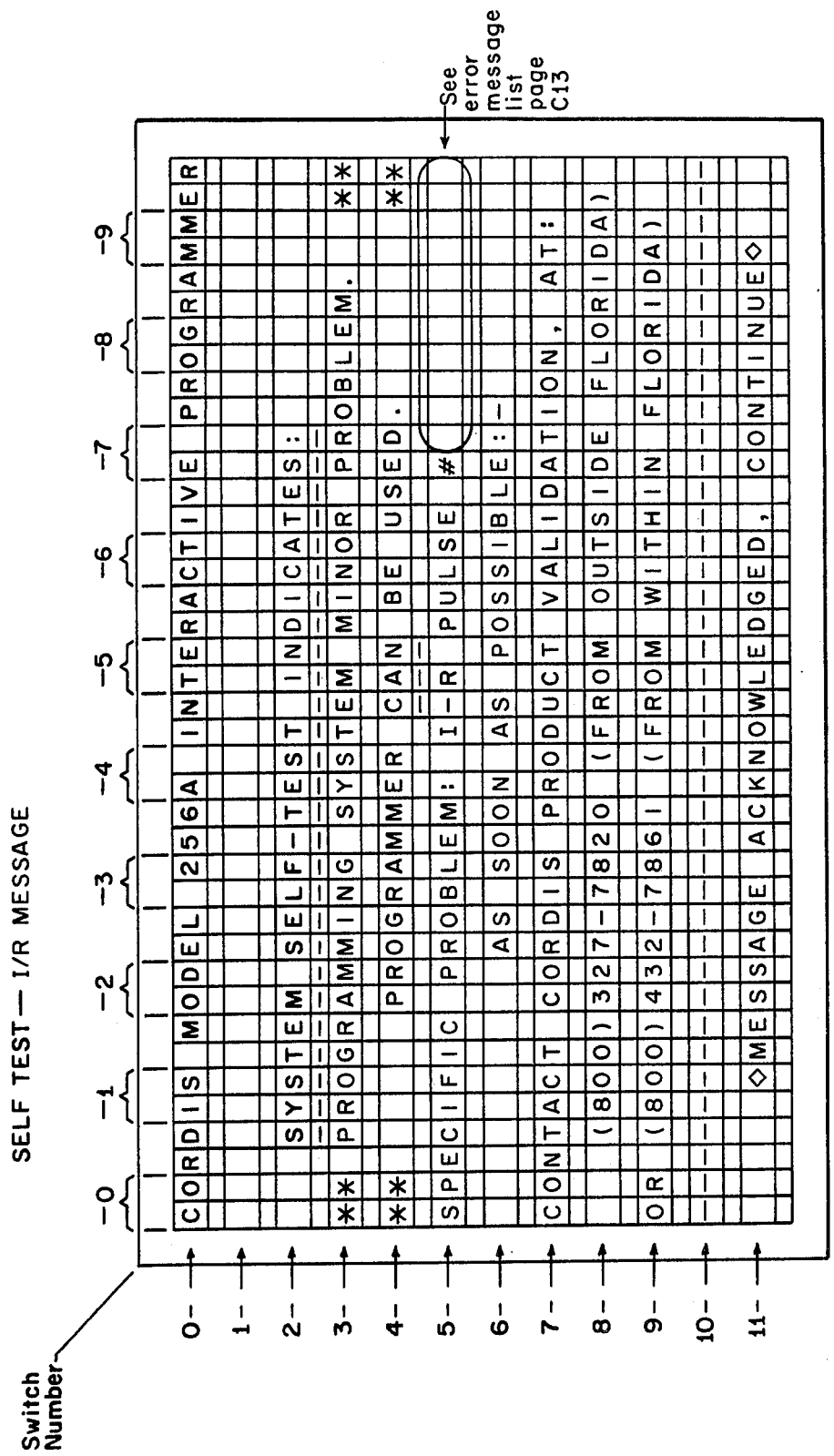

In the screen representations in the drawings, two asterisks indicate the beginning and the end of a portion of the display line which is blinking. FIG. 15C indicates the display screen message associated with a RAM failure. This is a serious system malfunction and the console beeps for two seconds and stops at this point in the operation. The same type of response occurs for malfunction in the read only memory test. At the start of the communications self test, the inability to obtain "acquisition" gives rise to the screen message in FIG. 15D. If the programming head is in fact in the cradle, the operator is instructed to press the diamond-shaped target after the sentence "If yes, press here." If the programmer is in the cradle and the operator presses the target but acquisition is still not obtained, the message of FIG. 15E is displayed, the console beeps for two seconds and the system stops at this point. If a problem appears in the magnetic programming pulses from the head during the communications self test, the message in FIG. 15F is displayed. To the right of the words "MAG PULSE", one of the possible eleven messages will appear concerning the condition of the first, second or third pulse:

1 Too late
1 Too soon
1 Too long
1 Too short
2 Too late
2 Too soon
2 Too long
2 Too short
3 Too late
3 Too soon
3 Too long
3 Too short The displays of FIGS. 15G and 15H illustrate the response to other variations in communications malfunctioning. Note that in the case of an IR pulse failure, the programmer can, of course, be used for programming non-IR implants such as the entire Omnicor line of cardiac pacers at present.

With reference again to the programming procedure of FIG. 14, after the self test routine is completed, which takes only a couple of seconds, the screen displays a choice between neural and cardiac pacer implants unless the internal DIP switch has been set to cardiac pacer preference in which case the next display will be that illustrated in FIG. 1 of all the programmable cardiac pacer models. Otherwise the display of FIG. 1 is selected by pressing a diamond-shaped target next to "Cardiac Pacer" (not shown). Each pacer model for which there is a programming routine in software will be preceded by a target. To access the programming routine for a given model, the operator presses the display target at the correct model number. Note that after the implant type has been selected, i.e., neural or pacer, the "stat set" standard parameters can be programmed at any time by removing the programming head from the console cradle, pressing the standard button on the programming head or the console, placing the programming head over the implant until acquisition is obtained and then while holding the programming head stationary, pressing and releasing the action button. This operation will automatically program the implant to standard nominally safe operating parameters. In the case of a neural implant, stat set turns the neural stimulator off. In the case of a cardiac paper, stat set chooses safe operation such as 70 bpm in the ventricular inhibited mode (VVI). The operator knows that the stat set values have been programmed successfully by the cessation of the audible tone which began with the pressing of the action button and the unlighting of the acquisition light on the programming head unless the console beeps and the message appears on the screen.

If the operator continues in the normal mode of reprogramming, the selection of a model number causes the display of a "menu" of programmable parameters and values. For example, FIG. 16A shows the display screen after selection of Model 162D Omni Stanicor. The proposed values are blank at first. The operator selects the values for the rate output and mode parameters by pressing one target beside the selected value for each one. If the operator selects 65 bpm at an output current of 4 milliamps in the asynchronous (VOO) pacing mode, the next display is as shown in FIG. 16B. Note that the displays in FIGS. 16A and 16B contain a target next to the words "list models". This enables the operator to go back to the model listing if desired. Of course, at this time or at any other time after the selection of the type of implant, the operator can "hit" the standard button in an emergency.

Next in the routine programming operation, the program target at the bottom of the screen in FIG. 16B is pressed by the operator. The screen changes to the display of FIG. 16C which while advising the operator of the proposed parameter values which he is going to program, instructs the operator to place the programming head 12 on the patient over the site of the OmniStanicor pacer and then depress and release the action button or to hit the target next to "cancel pending action". Next the operator following these instructions removes the programming head from the console cradle and moves it over the implant site until the "ACQ" light goes on. After the action button is released, the programmer automatically sends the prescribed number of magnetic impulses via the programming head to the implant in order to cause the implant to reprogram itself to the desired parameter values. The screen changes automatically to the display of FIG. 16D indicating that the present values match the proposed values, assuming that the implant has received the program correctly. At this point if the operator desires to reprogram any one or more of the parameters he simply selects and presses the target next to the value in FIG. 16D causing the proposed value slate to change. On the other hand, if the programming is satisfactory, the doctor presses the display target at print and the printer automatically prints out the format shown in FIG. 17. The data and time, model number, electrode location and programmed parameter values are automatically included. Spaces for the patient's name, serial number, operator, location, doctor and other remarks are provided on the printed record. After the printing is completed, the operator pushes the paper advance and tears off the paper tape, writes in whatever notations he desires, and places the tape in the patient's file as a permanent record of the programmed values of the patient's pacer. While the printing operation is taking place, the display screen includes the message "STOP PRINTING" with a target next to it.

For even more versatile pacers, such as Cordis Model 336 Multicor Gamma, a typical sequence of displays is shown in FIGS. 18A through 18H and a typical printout in FIG. 19. Because of the greater number of parameter values, the selection process is broken into two parts, the first of which as shown in FIG. 18A is to select the parameter and the second of which is to display the available values for the selected parameter, as on the right-half of the screen in FIG. 18B. As in the Omnicor programming, a value must be specified for each of the parameters before programming. In the Multicor pacer, the electrode can either be unipolar or bipolar and this information must be known by the physician before programming in order to avoid the possibility of an error in designating the ANODE. Thus before the display of FIG. 18A, the screen asks the operator to identify whether the electrode is unipolar or bipolar. After all of the values are designated for the programmable parameters of the Multicor, the display appears as in FIG. 18C. The right-half of the screen contains the action list which now includes the target next to the word "proposed". The proposed values are programmed by pressing the target and following the instructions in the ensuing display of FIG. 18D. As in the preceding example, the programming operation can be aborted by pressing the cancel action target. Following programming, if no further changes are desired, the print present target is pressed to generate the printout of FIG. 19.

Programming a Cordis Gemini pacer is illustrated below. The Gemini pacer output formation circuits, diagnostic circuitry and emergency system are disclosed in copening Applications Ser. Nos. 239,467 and 239,468. In addition, the Gemini pacer is equipped with telemetry of the type disclosed in U.S. Pat. No. 4,361,153 and copending application Ser. No. 195,665. Telemetry enables two-way communication between the programmer and the implant.

After the programmer has been turned on, the self test has been successfully completed and implant type (i.e., pacer) has been selected, the screen displays all of the programmable cardiac pacers by model number. Pressing the diamond shaped target beside the appropriate model number selects a corresponding programming routine and appropriate tables from EPROM. Assume the user or operator selects not one of the pacer models but instead hits the STAT SET button 72 on the programming head 12. This causes the display to blink the "Action pending—program standard" message. The user places the programming head over the implant and presses and releases the action button. The display informs the user that the programmer is not satisfied that the standard values have been programmed and directs the user to repeat the programming operation, which he does. Finally, the screen confirms that the standard values have been programmed and the user resumes the programming operation by pressing the target to list the models. Note that the programming of the standard value takes place before the programmer was advised of the pacer model number.

Continuing with the programming operation, the user selected Cordis model number 415, the Gemini pacer with two chamber, unipolar/bipolar lead and telemetry capabilities. The Gemini pacer is capable of being programmed in a wide variety of pacing modes. The next display occurring after the selection of the Gemini pacer instructs the user to interrogate the Gemini pacer to learn if the present values of its parameters. Instead, however, the user again hits the programming head standard button which halts the programming operation and displays guide and confirm the programming of the safe standard values. The display allows the user to go back to the model listing or continue with the interrogation. The interrogation instruction orders the user to hit the action button on the programming head. If acquisition had not first been obtained, the display would direct the user to repeat interrogation.

The interrogation operation is shown in FIG. 20. The microprocessor system 88 issues a string of binary pulse width modulated magnetic impulses via the programming transducer 200 in the programming head 12. In the implant the programming transducer 202, i.e. the magnetic responsive element such as a reed switch, receives the transmitted data and passes it into the computer system within the Gemini pacer which includes means 204 for checking the period, pulse widths and bit count of the command and means 206 for checking an identification code corresponding to the model number of the pacer. Finally, a program code checking operation 208 decodes the interrogation command and directs the implant's memory to output serially all stored parameter codes in binary pulse width modulated (i.e., long and short pulses) via the telemetry transducer 212 which is preferably a shorted coil transponder of the type disclosed in U.S. Pat. No. 4,361,153 and copending application Ser. No. 195,665. The parameter data is received by the telemetry transducer 214 in the programming head 12 and transferred to registers 216 for storing present values to which the implanted cardiac pacer is currently programmed.

The results of interrogation of a Gemini pacer, for example, are displayed for the following parameters: mode (meaning pacing mode such as VVI), rate, delay (i.e., AV delay), anode (whether one electrode of a bipolar lead or the pacer case), pace limit (whether on or off), electrode location and type for channel 1 and channel 2 (atrial or ventricular location and unipolar or bipolar electrode type), the refractory periods specified for channels 1 and 2 and the sensitivity and output on channel 1 and channel 2. Typically channel 1 and channel 2, of course, refer to atrium and ventricular. The sensitivity refers to the sensed voltage on the pacer lead resulting from natural cardiac activity in order to inhibit pacer action. Assume the sensitivity is OFF corresponding to infinite threshold on channel 1. The output intensity is specified in terms of paired amplitude and pulse width. Assume, for example, the interrogated values are an amplitude of two milliamps on channel 1 and 0.2 milliseconds pulse width and on channel 2 and amplitude of ten milliamps and 1.0 milliseconds. Output intensities are programmed in predetermined pairs of pulse width and amplitude arranged in a monotonically increasing series as disclosed in copending Application Ser. No. 239,468. Note that if the electrode location and type are not specified for either channel, this condition results in the mode being indeterminate. Before any further programming other than the standard values can take place, the right-half of the screen only permits the operator to specify the location and type for the channel 2 electrode. Targets are not presented along side any of the other parameters on the left-hand half of the Gemini display. In response to the electrode uncertainty, the user selects ventricular location and unipolar type electrode for channel 2 by pushing the target on the screen next to VU. In response the letters "PROP" appear beside the electrode selection and the designation VU appers on the left-hand side of the screen. Note that this is not a programming operation. No change is effected in terms of control of the pacer parameters directly. However, this information will be transmitted to the pacer for storage in the pacer's memory. In addition to the location and unipolar/bipolar type of electrode, the electrode type may be designated as "shared" in which case the electrodes share a common annode. Following designation of the electrode, targets appear beside all of the parameters on the left-hand side of the display screen allowing the user to now propose new values. In addition, having "located" the channel 2 electrode in the ventricle, the mode is clarified to "VVI". The proposed designation or parameter value is underlined on the left-half of the screen. The underline is not removed until the pacer has been programmed.

Next, the user presses the target beside "GO TO ACTION LIST" and generates a display which only changes the right-half of the display to indicate various action options. Assume the user selects the program diagnostic mode. The diagnostic mode automatically selects asynchronous mode (VOO) of fifty-three beats per minute. The diagnostic mode assumes that the channel 2 electrode is connected to the ventricle. After confirming programming of the diagnostic mode, the display allows the user to cancel the diagnostic mode and display various options. Diagnostic mode is cancelled by following the displayed instructions.

Following a number of other consecutive illustrations, the hypothetical user returns to the proposed value chart and continues to designate parameter values by pressing the target next to electrode in the column for channel 1. This generates the electrode menu on the right-half of the display from which the user, for example, selects an atrial unipolar shared designation. This selection forces the channel 2 electrode to "A U SH" as well. Attempts by the operator to designate channel 2 as something other than "A U SH" fail and the user will realize that he should have selected a "A U" for the channel 1 electrode. Next, if the user were to attempt to change the annode from the case to an electrode, the display would remind him that electrodes should only be chosen to provide polar lead as used. If the user selects a parameter to program which he then decides not to program, he need not select one of the available values for the parameter but can immediately select a different parameter. The annode may correctly be designated as the case since the channel 2 electrode is bipolar. Mode selection is made. The user's attempt to program the anode to electrode in a pacer where a bipolar channel 2 electrode designation fails. Programming of adverse relationships between rate and refractory period is inhibited by software within the programmer. The paired output parameters are listed. Finally, after all of the parameter values have been proposed to the operator's satisfaction, the user goes to the action list and selects program proposed. Following the displayed instructions, the user places the programming head over the Gemini pacer and presses and releases the action button.

The ensuing programming operation is diagrammed in FIG. 21. The proposed values displayed on the left-half of the display are contained in proposed value registers 222 of the microprocessor system 88 in the programmer. When the action button is activated after acquisition of the implant, the proposed values are serially output via the programming transducer 200 in the head 12 in the pulse width modulated magnetic form. The binary string contains the proposed values which are underlined on the left-half of the screen. The incoming pulse string is received by the programming transducer 202 and check means 204, 206 and 208 in the implanted pacer. In addition the parameter code is subjected to an additional check 218. Verifying the programming data, the operating memory 210 of the pacer loads the desired parameter codes and automatically echoes out in serial fashion the new parameter codes via the telemetry transducer 212. The programmer receives the echo; software means 220 in the programmer verifies the echo and compares the data string received from the implant with proposed value registers for contradictions.

Finally, after lowering the rate parameter from 125 beats per minute to 80 beats per minute, the user succeeds in programming the implant to full atrial and ventricular inhibited AV sequential operation. The right-half of the display contains an action list from which the user may select "PRINT PRESENT". The printer sub-routine serves the correct parameter values and model numbers to the printer system which adds the date and time, creating the printout.

The foregoing display scenarios were designed to illustrate various programming modes and interactions with the user. In particular, with respect to the Gemini scenario, programming would actually be more straightforward without the deliberate missteps taken in the scenario to illustrate the response of the programmer. The system can be modified to accommodate new biomedical implants such as new types of pacers and new parameter values and even new parameters. Versatility is the hallmark of the interactive programmer. The system is not limited to the type of display and user input (overlay switch matrix) disclosed in this application. For example, a CRT or equivalent screen-type display could be substituted; and instead of the transparent touch sensitive switch matrix, other types of two dimensional screen inputs such as light pens or other types of mechanical switch arrays can be substituted. The use of dual acquisition lights is optional as is the printer, calendar clock and other features of the interactive programmer. Since all of the user interactions, display messages and formats, scenarios and programming outputs and alarms are on software, they can be changed by reprogramming the appropriate EPROM's without changing any of the hardware of the interactive programmer. The overall system is not limited by design to the use of any specific computer circuitry, memory capacity or I/O capacity, although the disclosed CDP 1802-based system is presently preferred. The communication self test system is, of course, not limited in concept to any specific media. Ultrasound or RF communication systems can be accommodated by the use of appropriate transducers in the self test module within the programmer.

Besides its versatility, the interactive programmer for the first time provides the medical community with an intelligent programming console which not only prompts the operator but corrects and explains inappropriate commands by the user to achieve an unprecedented degree of cooperation between the programming console, the implant and the physician. Safety is enhanced by the ability to lock out forbidden modes and potentially disadvantageous combinations of parameters by means of software. The addition of telemetry capability assures the physician that the implant's registers have in fact received the correct data by verifying the automatic echo of a full transmitted string upon receipt by the implant. The important concept of limited access implies that a single console may have different capabilities for different operators. That is, it may be given a hierarchy of parameter access levels dependent upon the "security clearance" of the operator. The automatic printer relieves the operator of the responsibility for recording correctly the programmed parameters. This feature is particularly important for nontelemetry pacers where in the past, the only means of determining the present values of parameters were indirect by way of inference from the magnet rate EKG, in the absence of reliable records.

The foregoing description, appendices and drawings are intended to be illustrative only rather than restrictive, the scope of the invention being indicated by the appended claims.

What is claimed is:

1. An interactive programmer console for programming implantable biomedical devices by enabling the operator to select among a number of parameter options including parameters and parameter values and then executing the reprogramming of the implant in accordance with the selected parameter options, comprising
   a display screen,
   a transparent switch matrix sheet covering said screen and having a plurality of transparent touch sensitive switch locations of undefined functionality distributed over the surface of the screen,
   means for displaying on said screen a selectable set of parameter options by simultaneously generating a plurality of parameter option messages on the screen with juxtaposed targets over corresponding arbitrary switch locations so as to define the functionality of the corresponding set of switch locations,
   means responsive to operator actuation of any switch location for ignoring such actuation unless a target is present at such location,
   means responsive to operator actuation of a switch location at a target on said screen for registering the selected parameter option indicated by the juxtaposed message on the screen,
   memory means for addressably storing and retrieving parameter data, and
   means responsive to an operator command for encoding and transmitting parameter data from said memory means corresponding to at least one parameter option selected by actuation of the temporarily corresponding switch, in a form capable of being received and decoded by said implant for executing the reprogramming of said implant in accordance with the selected parameter option,
   whereby individual switch locations in said switch matrix can be redefined under control of the screen to designate different functions to accommodate different sets of programmable options.

2. The console of claim 1, further comprising
   means for displaying on said screen a plurality of implant identification codes and for indicating a correspondence between said switch locations and said implant identification codes, and
   means responsive to operator actuation of said switch matrix means at a selected one of said switch locations for obtaining from memory all parameter data options associated with the selected implant.

3. The console of claim 2, further comprising means responsive to an operator command for displaying on said screen a set of programmable parameters for the selected implant and indicating a correspondence between a certain ones of said switch locations and said parameters, and
   means responsive to operator actuation of said switch matrix means at one of said switch locations for displaying on said screen the optional values for the selected parameter and indicating a correspondence between a certain ones of said switch locations and said values.

4. The console of claim 3, further comprising
   means for indicating while displaying the optional values for said selected parameter the present value to which said parameter is programmed in the implant.

5. The console of claim 1, further comprising
   logic means for determining inconsistent choices among parameter values for a given implant and for responding to operator actuation of said switch matrix at a selected location which would result in an inconsistent parameter choice by disallowing the obtaining of the inconsistent parameter data from said memory means and for displaying an explanation on said screen.

6. The console of claim 1, further comprising
   means responsive to operator selection of an implant with telemetry for interrogating the implant via telemetry to ascertain its present parameter values,
   means for storing and displaying on said screen said present parameter values, and
   means for inhibiting selection of parameter data by the operator which conflicts with the present stored parameter data.

7. The console of claim 1, further comprising
   coded access switch means assuming one or the other state in response to the setting of a predetermined coded value by the operator, and
   means for limiting access to certain parameter data in said memory means in accordance with said coded access switch means state.

8. The console of claim 1, further comprising
   means for identifying on said screen the switch location for a set of standard values of parameters,
   said memory means containing an addressable set of standard parameter values,
   means responsive to actuation of said switch matrix at the switch location identified for standard values for obtaining said standard value set from said memory means and executing reprogramming in accordance therewith.

9. The console of claim 8, further comprising
   said memory means having means for storing at least two mutually exclusively addressable sets of standard parameter values for different respective generic types of implants,
   means responsive to operator selection of the generic type of implant for limiting the addressability of the standard values in said memory means to the corresponding set.

10. The console of claim 8, further comprising
    a movable programming head containing a programming transducer system coupled with the remainder of said programming console and having an auxiliary standard switch,
    said means for obtaining said standard values from said memory means being further responsive to actuation of said standard switch on said programming head.

11. The console of claim 1, wherein said display is a two-dimensional, multiple line, alpha numeric character display and said switch matrix means switch locations having outputs corresponding to responsive rows and columns of said switch matrix.

12. The console of claim 1, further comprising
lockout means for omitting the target from an otherwise available parameter option in accordance with a predetermined condition,
whereby a conflicting parameter option can be rendered impermissible via the screen so as to ignore the actuation of the corresponding switch.

13. An interactive programmer console for programming implantable biomedical devices having telemetry systems by enabling the operator to select among a number of programming choices and then executing the reprogramming of the implant in accordance with the selected parameter data, comprising
memory means for addressably storing and retrieving parameter data,
operator interface means for specifying desired parameter data,
means responsive to said operator interface means for obtaining corresponding data from said memory means,
means responsive to an operator command for encoding and transmitting said parameter data in a form capable of being received and decoded by said implant for executing the reprogramming of said implant to the desired parameters and values,
means for receiving telemetry data from said implant indicative of the parameter data presently controlling the implant,
means in said console for automatically testing both the transmitting and telemetry receiving means in a two-way communications sequence,
a tabletop console and a movable handheld programming head containing said transmitting means and said telemetry receiving means and electrically coupled to said console, said console having a programming head cradle, and
a self test module mounted in said console adjacent to said cradle for performing two-way communication with said programming head.

14. The console of claim 13, wherein said self test module includes means for receiving data transmitted from said programming head transmitting means, means for storing said received data and means for retransmitting said stored received data in a form receivable annd decodable by said telemetry receiving means of said programming head.

15. The console of claim 14, wherein said programming head transmitting means includes means for transmitting in a first medium and means for transmitting in a second medium, said self test module receiving means including means for receiving transmission in said first medium and means for receiving transmission in said second medium.

16. The console of claim 15, further comprising
means for causing said programming head to transmit a test signal to said self test module in said first transmission medium followed by transmission of a test signal to said self test module in said second medium.

* * * * *